US012606502B2

(12) United States Patent
Yang et al.

(10) Patent No.: US 12,606,502 B2
(45) Date of Patent: Apr. 21, 2026

(54) METHOD FOR PREPARING P-XYLENE BY BIOMASS CONVERSION

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Weimin Yang, Shanghai (CN); Xiangcheng Li, Shanghai (CN); Zhendong Wang, Shanghai (CN); Xinqiang Feng, Shanghai (CN); Xiao Han, Shanghai (CN); Rui Xu, Shanghai (CN); Chuang Liu, Shanghai (CN); Zhiqing Yuan, Shanghai (CN); Jian Qiao, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 235 days.

(21) Appl. No.: 18/561,473

(22) PCT Filed: May 20, 2022

(86) PCT No.: PCT/CN2022/094003
§ 371 (c)(1),
(2) Date: Nov. 16, 2023

(87) PCT Pub. No.: WO2022/242731
PCT Pub. Date: Nov. 24, 2022

(65) Prior Publication Data

US 2024/0254064 A1 Aug. 1, 2024

(30) Foreign Application Priority Data

May 21, 2021 (CN) ......................... 202110559517.4
May 21, 2021 (CN) ......................... 202110559519.3
Oct. 22, 2021 (CN) ......................... 202111233104.3

(51) Int. Cl.
*C07C 2/52* (2006.01)
*B01J 29/04* (2006.01)
*B01J 29/83* (2006.01)

(52) U.S. Cl.
CPC ............... *C07C 2/52* (2013.01); *B01J 29/047* (2013.01); *B01J 29/83* (2013.01)

(58) Field of Classification Search
CPC .. C07C 2/52; C07C 2/86; C07C 2/865; C07C 2/867; C07C 2/88; C07C 2529/70;
(Continued)

(56) References Cited

U.S. PATENT DOCUMENTS 10,974,967 B2 * 4/2021 Yang ........................ B01J 29/04
11,097,256 B2 * 8/2021 Yang ..................... C01B 37/007
(Continued)

FOREIGN PATENT DOCUMENTS

CN 102482177 A 5/2012
CN 102596866 A 7/2012
(Continued)

OTHER PUBLICATIONS

Feng, Xinqiang et al.; "Is Hydrolysis a Bad News for p-Xylene Production from 2 , 5-Dimethylfuran and Ethylene? Mechanism Investigation into the Role of Acid Strength During 2 , 5-Hexanedione Conversion", Journal of Catalysis, vol. 401, Aug. 2, 2021; ISSN:0021-9517; pp. 214-223.
(Continued)

*Primary Examiner* — Youngsul Jeong
*Assistant Examiner* — Jason Y Chong
(74) *Attorney, Agent, or Firm* — NKL Law; Allen Xue

(57) ABSTRACT

A method for preparing paraxylene by biomass conversion includes the following steps: (1) contacting a biomass starting material with a hydrogenation catalyst for reaction in a multiphase system formed by an organic solvent, an inorganic salt and water, in the presence of hydrogen as a hydrogen source, and separating the resulting product to obtain an organic phase comprising 2,5-hexanedione; and
(Continued)

(2) contacting the organic phase comprising 2,5-hexanedione obtained in the step (1) and ethylene with a molecular sieve catalyst for reaction to obtain paraxylene. The molecular sieve catalyst is at least one selected from the group consisting of aluminophosphate molecular sieves and SCM-14 molecular sieves.

21 Claims, 10 Drawing Sheets

(58) Field of Classification Search
CPC ....... C07C 2529/84; C07C 45/60; C07C 1/20; C07C 15/08; B01J 29/83
See application file for complete search history.

(56) References Cited

U.S. PATENT DOCUMENTS

| | | | | |
|---|---|---|---|---|
| 2010/0331568 | A1* | 12/2010 | Brandvold | C07C 2/86 585/408 |
| 2013/0245316 | A1* | 9/2013 | Masuno | C07C 51/16 585/409 |
| 2014/0296600 | A1* | 10/2014 | Dauenhauer | C07C 2/865 585/469 |
| 2019/0031579 | A1* | 1/2019 | Liu | C07C 2/867 |

FOREIGN PATENT DOCUMENTS

| | | | |
|---|---|---|---|
| CN | 103814005 | A | 5/2014 |
| CN | 109081359 | A | 12/2018 |
| CN | 109081360 | A | 12/2018 |
| CN | 111004078 | A | 4/2020 |

OTHER PUBLICATIONS

Feng, Xinqiang; "Catalytic Production of p-Xylene From 2,5-Dimethylfuran/2,5-Hexanedione and Ethylene Over Solid Acid", Chinese Doctoral Dissertations Full-text Database(Ph.D) Engineering Science and Technology Series I); No. 03, Mar. 15, 2022; ISSN: 1674-022X; pp. 1-154.

Williams, C. Luke et al.; "Cycloaddition of Biomass-Derived Furans for Catalytic Production of Renewable p-Xylene"; ACS Catalysis; Feb. 2012; pp. 935-939.

Date, Nandan S. et al.; "Single pot selective hydrogenation of furfural to 2-methylfuran over carbon supported iridium catalysts"; Green Chemistry; vol. 20; Year: 2018; pp. 2027-2037.

Faria, Jimmy et al., "Carbon Nanotube/Zeolite Hybrid Catalysts for Glucose Conversion in Water/Oil Emulsions", ACS Catalysis, vol. 5, No. 8, Jul. 16, 2015, pp. 4761-4771.

* cited by examiner

METHOD FOR PREPARING P-XYLENE BY BIOMASS CONVERSION

TECHNICAL FIELD

The present application relates to the field of catalytic chemistry, and particularly to a method for preparing paraxylene by biomass conversion, especially to a two-step method for preparing paraxylene by biomass conversion.

BACKGROUND ART

With the progress of science and technology and the development of society, the demand of human beings on traditional fossil energy such as coal, petroleum, natural gas and the like is more and more increased, so that the reserves of the fossil energy on the earth are exhausted day by day, and the combustion of the fossil energy will seriously pollute the environment; in contrast, biomass is a green renewable energy source, of which the reserves on earth are abundant, and the conversion and utilization will not pollute the environment, so that many researchers aim at supplementing fossil energy sources with biomass. Para-xylene (pX) is a very important chemical raw material, and the main purpose of the para-xylene (pX) is to produce polymer monomer products such as terephthalic acid, terephthalate and the like. pX is currently produced mainly from the petrochemical route, but the traditional pX production route based on petroleum feedstocks leads to environmental degradation and increases carbon dioxide emissions.

The preparation of pX from biomass-based sources has gradually become a research focus in recent years. CN102596866A discloses a method for producing para-xylene from biomass, which comprises fermenting biomass having been treated to provide a fermentation feedstock with a microorganism capable of producing isobutanol, dehydrating isobutanol to isobutene, dimerizing, and then subjecting to dehydrocyclization to produce pX. This fermentation method for preparing pX has the disadvantages of long fermentation time, multiple reaction steps, high cost, difficulty in product separation and low economic value. Meanwhile, the Dauenhauer topic group (ACS Catal. 2012, 2, 935-939) proposed to produce pX from 2,5-dimethylfuran (DMF) through Diels-Alder and dehydration reaction routes. The results show that when the H—Y molecular sieve is used as a catalyst, the pX selectivity is only 75% when the reaction is carried out at a temperature of 300° C., a large amount of alkylbenzene is generated, the cost for purifying and separating the product is increased, and thus the requirement of large-scale production is difficult to be met.

The research on the technical route for preparing pX from 2,5-dimethylfuran is progressed well, wherein the 2,5-dimethylfuran is prepared by hydrogenolysis of fructose or 5-hydroxymethylfurfural mainly under the catalytic action of noble metals, but conventional production methods usually have the problems of high raw material cost, short catalyst life and the like, so that the price of DMF is high, and the economical efficiency of the technical route for preparing pX from DMF is limited. Existing biomass-based pX production methods have the problem of long reaction path, and high cost, of which the large-scale application is difficult to realize. Therefore, an efficient and green method for preparing paraxylene by catalytic conversion of biomass is needed, by which biomass raw materials such as cellulose and glucose can be efficiently converted into pX.

Alternative methods for the production of toluene from the reaction of biomass-derived methylfurans (MF) with ethylene have also been under research. Furfural can be prepared from biomass by hydrolytic dehydration and can be converted into methylfuran by further hydrogenolysis (Green chemistry. 2018, 20, 2027-2037). The prior experiment results show that the effect is best when H-Beta molecular sieve is used as a catalyst. The toluene selectivity is only 46% at the highest when the reaction is carried out at a temperature of 250° C., and a large amount of polymer is generated, so that the cost for purifying and separating the product is increased, and the requirement of large-scale production is difficult to be met.

Meanwhile, pure ethylene is adopted as a raw material in the above reported experiments, but dilute ethylene in refinery fluid catalytic cracking dry gas is difficult to utilize due to the low concentration (10(v)-25 (v) %), so that the dilute ethylene is generally used as a fuel to be burnt in the past, causing a waste of precious resource. If this part of ethylene resource can be effectively utilized, high-value conversion of dilute ethylene resources may be realized, and a wide development prospect particularly in the preparation of biomass-derived chemicals may be expected.

DISCLOSURE OF THE INVENTION

The present application aims to solve the technical problems of low catalytic efficiency, multiple reaction steps, long time, high cost, environmental pollution and the like in the production of substituted or unsubstituted monocyclic aromatic hydrocarbons such as toluene, paraxylene and the like in the prior art, and provide a method for preparing the substituted or unsubstituted monocyclic aromatic hydrocarbons such as toluene, paraxylene and the like by biomass conversion. The method is simple to operate, has the advantages of high product selectivity, good catalyst stability, easy product separation, few reaction steps and short time, and may achieve a green and efficient conversion of biomass.

As a result of intensive studies, based on a technical route for preparing pX from 2,5-dimethylfuran and a technical route for preparing toluene from methylfuran, the inventors found that SCM-series molecular sieves, such as SCM-14 and SCM-15, have excellent catalytic effects on both the addition reaction and dehydration reaction of furan having a methyl substituent, which are supposed to occur. Further, SCM series molecular sieves, such as SCM-14 and SCM-15, also exhibit excellent catalytic effects for the dehydration of 2,5-hexanedione to 2,5-dimethylfuran.

To solve the above technical problems, the present application provides embodiments of various aspects.

In an embodiment, a first aspect of the present application provides a method for preparing a substituted or unsubstituted monocyclic aromatic hydrocarbon from a substituted or unsubstituted furan, comprising:

- contacting an organic phase comprising a substituted or unsubstituted furan as starting material with ethylene and a molecular sieve catalyst for reaction to obtain a substituted or unsubstituted monocyclic aromatic hydrocarbon,
- wherein the molecular sieve catalyst comprises an SCM-X molecular sieve optionally doped with an element A that is at least one selected from the group consisting of Sn, Zr and Al, and X is 14 or 15.

In an embodiment, the SCM-X molecular sieve has a schematic chemical composition represented by the formula "$mSiO_2 \cdot nGeO_2$": wherein $1 \leq m/n \leq 30$, preferably $0.5 \leq m/n \leq 20$, further preferably $2 \leq m/n \leq 10$.

In an embodiment, the organic phase comprises an organic solvent selected from the group consisting of n-hexane, n-heptane, n-octane, tetrahydrofuran, 1,4-dioxane, cyclohexane, and methyl isobutyl ketone.

In an embodiment, the substituted or unsubstituted furan used as starting material has a structure represented by formula (I) below:

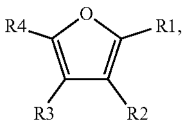

(I)

wherein R1, R2, R3 and R4 are each independently selected from H and C1-C6 alkyl, preferably each independently selected from H and C1-C4 alkyl, and further preferably at least one of R1, R2, R3 and R4 is not H;

with a proviso that the total number of carbon atoms of R1, R2, R3 and R4 is not greater than 8, preferably not greater than 6.

In an embodiment, the substituted or unsubstituted furan is methylfuran and the substituted or unsubstituted monocyclic aromatic hydrocarbon is toluene.

In an embodiment, the substituted or unsubstituted furan is 2,5-dimethylfuran and the substituted or unsubstituted monocyclic aromatic hydrocarbon is paraxylene.

Based on the method for preparing a substituted or unsubstituted monocyclic aromatic hydrocarbon from a substituted or unsubstituted furan of the first aspect of the present application, a second aspect of the present application further provides a method for preparing paraxylene from 2,5-hexanedione, comprising:

contacting an organic phase comprising 2,5-hexanedione and ethylene with a molecular sieve catalyst for reaction to produce paraxylene, wherein the molecular sieve catalyst comprises an SCM-X molecular sieve, and X is 14 or 15;

preferably, the SCM-X molecular sieve is an SCM-14 molecular sieve having a schematic chemical composition represented by the formula "$SiO_2 \cdot 1/nGeO_2$", where $n \leq 30$, preferably $0.5 \leq n \leq 20$, more preferably $1 \leq n \leq 10$, and more preferably $2 \leq n \leq 8$.

In an embodiment, the ethylene pressure is from 0.5 to 5 MPa, preferably from 1 to 4 MPa; and/or the reaction temperature is 160-340° C., preferably 200-300° C.; and/or the reaction time is 6-64 h, preferably 12-48 h.

Further, based on the method for preparing paraxylene from 2,5-hexanedione of the second aspect of the present application, a third aspect of the present application provides a method for preparing paraxylene by biomass conversion, comprising the following steps:

(1) contacting a biomass starting material with a hydrophobic hydrogenation catalyst for reaction in a two-phase solvent system comprising an organic solvent phase and an aqueous solution phase, in the presence of hydrogen as a hydrogen source, and separating the resulting product to obtain an organic phase comprising 2,5-hexanedione; wherein the pH of the aqueous solution phase is about 6.5-8.5, preferably 7-8;

(2) contacting the organic phase comprising 2,5-hexanedione obtained in the step (1) and ethylene with a molecular sieve catalyst for reaction to obtain paraxylene, wherein the molecular sieve catalyst is at least one selected from the group consisting of an aluminophosphate molecular sieve and an SCM-14 molecular sieve.

According to the present application, step (1) is carried out by a batch reaction. Preferably, the pH of the aqueous solution phase in step (1) is the pH as measured in the two-phase solvent system before the start of the reaction.

According to the present application, the biomass starting material used in the step (1) is one or more selected from the group consisting of cellulose, inulin, cellobiose, sucrose, glucose, fructose, corn straw, corncob, pine wood, poplar wood and beech wood, preferably cellulose and/or glucose.

According to the present application, preferably, the aqueous solution phase in step (1) comprises an inorganic salt dissolved therein, the anion and cation of said inorganic salt being derived from a Group VIIA element and a Group IA element, respectively, wherein the Group VIIA element is at least one selected from the group consisting of Cl and Br, and the Group IA element is at least one selected from the group consisting of Li, Na, K.

In an embodiment, the inorganic salt is chloride or bromide. For example, the inorganic salt may be LiCl, NaCl, KCl, LiBr, NaBr, or KBr.

In existing methods for preparing paraxylene by biomass conversion in the art, liquid acid or acidic salt is typically added into the reaction system for the step of producing 2,5-hexanedione from biomass, so as to exert a catalytic effect together with a supported noble metal. That is, in known conventional processes, an acidic reaction environment is typically maintained. Without being bound to any known theory, the inventors have made an in-depth research and found that excellent reactivity can be obtained in the presence of a supported noble metal when a certain concentration of an inorganic salt of a halogen element is introduced and maintained in the reaction system and the reaction system is maintained at an approximately neutral pH.

According to the present application, the ratio of the mass of the organic solvent to the total amount by mass of the inorganic salt and water is between 2 and 16, preferably between 3 and 10; and/or the ratio of the mass of the inorganic salt to the mass of the water is 0.10 to 0.70, such as but not limited to 0.10, 0.20, 0.30, 0.40, 0.50, 0.60, 0.70 or a range formed between any two of them, preferably 0.20 to 0.70, more preferably 0.40 to 0.70. In the present application, when the ratio of the mass of the inorganic salt to the mass of the water is 0.40 higher, a more prominent effect of improving the selectivity of the 2,5-hexanedione product can be achieved in the presence of the hydrophobic catalyst of the present application.

According to the present application, the hydrogenation catalyst used in step (1) comprises a hydrogenation active component and a carrier.

According to the present application, the carrier is one or more selected from the group consisting of activated carbon and graphene having hydrophobicity.

According to the present application, the hydrogenation active component is one or more selected from the group consisting of ruthenium, platinum and palladium, and preferably platinum and/or palladium.

According to the present application, the mass content of the hydrogenation active component, calculated on the basis of metal atom, is 0.5-10%, preferably 2-6% based on the mass of the hydrogenation catalyst.

According to the present application, the mass content of the carrier is 90-99.5%, preferably 94-98%, based on the mass of the hydrogenation catalyst.

According to the present application, the contact angle of the hydrogenation catalyst with water is greater than 50°, preferably between 55° and 90°, such as but not limited to the following values: 55°, 60°, 65°, 70°, 75°, 80°, 85°, 90°.

According to the present application, the organic solvent used in the step (1) is one or a mixture of two or more of 1,2-dichloroethane, 1,4-dioxane, methyl isobutyl ketone, tetrahydrofuran, γ-valerolactone and toluene, and preferably one or two of 1,4-dioxane and tetrahydrofuran.

According to the present application, the mass ratio of the organic solvent to the biomass starting material is between 4 and 60, preferably between 10 and 40.

According to the present application, the mass ratio of the biomass starting material to the hydrogenation catalyst used in step (1) is in a range of from 0.2:1 to 4:1, preferably in a range of from 0.5:1 to 2:1.

According to the present application, in the step (1), the reaction temperature is 160-250° C., preferably 180-230° C.; the reaction time is 4 to 36 hours, preferably 6 to 20 hours.

According to the present application, in the reaction system of the step (1), the pressure of hydrogen is 0.2-5 MPa, preferably 0.5-3 MP a.

According to the present application, the product obtained by the reaction in step (1) is separated by centrifugation, so as to separate the organic phase comprising 2,5-hexanedione, i.e. the phase mainly comprising 2,5-hexanedione and the organic solvent. The organic phase comprising 2,5-hexanedione obtained in the step (1) is not required to be further separated, and is directly used as the starting material of the step (2), so that the step of further purifying and separating the 2,5-hexanedione is avoided.

According to the present application, the carrier in step (1) can be a hydrophobic carrier prepared using a high-temperature calcining method, which specifically comprises the following steps:

subjecting activated carbon and/or graphene to calcining at high temperature using an inert gas as a carrier gas, to obtain the hydrophobic carrier. The conditions of the high-temperature calcining include: a calcining temperature of 400-900° C. and a calcining time of 3-12 hours.

According to the present application, the hydrogenation catalyst used in step (1) can be prepared by an impregnation method (preferably an isovolumetric impregnation method), which specifically comprises the following steps:

impregnating a carrier with a solution containing a hydrogenation active metal, drying, calcining and reducing, to obtain the hydrogenation catalyst. The solution containing the hydrogenation active metal can be prepared using soluble metal compounds, such as nitrate, chloride, acetate, chloroplatinic acid and the like. The impregnation conditions are not particularly limited in the present application, and the impregnation may be carried out at room temperature for 1 to 10 hours, for example. The drying can be carried out in a conventional manner, preferably: the drying temperature is 40-90° C., and the drying time is 4-12 hours. The calcination may be carried out in a conventional manner, preferably: the calcining temperature is 300-550° C., and the calcining time is 3-8 hours. The reduction can be carried out using hydrogen, and the reduction conditions preferably include: a reduction temperature of 300-450° C., and a reduction time of 3-6 hours.

According to the present application, the aluminophosphate molecular sieve catalyst used in the step (2) is an M-AlPO molecular sieve catalyst, wherein M is a metal and is at least one selected from Co, Mg, Zn and Sn, and the AlPO molecular sieve is at least one selected from AlPO-17, AlPO-5, AlPO-8, AlPO-11 or AlPO-18, preferably at least one selected from AlPO-17 and AlPO-5. Further, the content of metal in the M-AlPO molecular sieve is not less than 0.2 wt %, and preferably 0.2 wt % to 2.0 wt %.

According to the present application, the M-AlPO molecular sieve has a schematic chemical composition represented by the formula "$mP_2O_5 \cdot nAl_2O_3 \cdot pMO_x$", wherein: $0.5 \le m/n \le 2$, and $20 \le m/p \le 300$; preferably $0.8 \le m/n \le 1.2$, $40 \le m/p \le 200$, x being the total number of oxygen atoms required to satisfy the valence of M.

According to the present application, the properties of the M-AlPO molecular sieve include: a total acid content of 100-500 $\mu mol \cdot g^{-1}$, preferably 150-400 $\mu mol \cdot g^{-1}$, and further preferably 250-400 $\mu mol \cdot g^{-1}$, wherein the weak acid content is not less than 55%, preferably 60%-80%, further preferably 60%-75%, and the strong acid content is not greater than 35%, preferably 5%-30%, and further preferably 10%-25%.

According to the present application, the method for preparing the M-AlPO molecular sieve comprises the following steps:

uniformly mixing a phosphorus source, an aluminum source, a metal source, a template agent and water to form a gel, then carrying out hydrothermal crystallization, washing, drying and calcining to obtain the M-AlPO molecular sieve.

According to the present application, the molar ratio of phosphorus source (calculated as $P_2O_5$), aluminum source (calculated as $Al_2O_3$), metal source (calculated as $MO_x$), template and water is 1:0.5-2.2:0.002-0.03:0.7-1.3:30-80.

According to the present application, the phosphorus source may be phosphoric acid. The aluminum source may be aluminum isopropoxide. The template agent is at least one selected from the group consisting of cyclohexylamine, tetrapropylammonium bromide, tetrapropylammonium hydroxide, tetraethylammonium bromide, tetraethylammonium hydroxide, triethylamine, n-butylamine, di-n-propylamine, diisopropylamine, ethylenediamine and ethylamine. The water is preferably deionized water.

According to the present application, the metal source is at least one selected from the group consisting of M-containing organic metal complexes, M metal salts and M metal hydroxides; for example, when M is cobalt, the cobalt source is at least one selected from the group consisting of cobalt nitrate, cobalt chloride, cobalt phosphate, cobalt potassium cyanide, cobalt oxalate, cobalt acetate, cobalt acetylacetonate, and N,N-bis(salicylaldehyde) ethylenediamine cobalt, and preferably at least one of cobalt phosphate and N,N-bis (salicylaldehyde) ethylenediamine cobalt.

According to the present application, the crystallization temperature of the crystallization is 160-240° C., preferably 180-220° C.; and/or the crystallization time is 0.5-144 h, preferably 1-120 h.

According to the present application, in the method for preparing the M-AlPO molecular sieve, the washing, the drying and the calcining can be carried out in a conventional manner, for example, the washing can be carried out by washing with deionized water, the drying can be carried out at 50-90° C. for 4-12 hours, the calcining can be carried out at 650° C. for 1-12 hours, and the calcining atmosphere is oxygen or air.

According to the present application, the SCM-14 molecular sieve and the method for its preparation are further described in Chinese patent No. CN 109081360B, the contents of which are incorporated herein by reference in their entirety.

According to the present application, the SCM-14 molecular sieve has a schematic chemical composition represented by the formula "$SiO_2 \cdot 1/nGeO_2$", wherein the silicagermania molar ratio n (representing $SiO_2/GeO_2$ molar ratio) is n≤30, preferably 0.5≤n≤20, more preferably 1≤n≤10, more preferably 2≤n≤8. Within this range, non-limiting values of the $SiO_2/GeO_2$ molar ratio can be 2.0, 2.5, 3.0, 3.5, 3.6, 3.7, 3.8, 4.0, 4.5, 5.0, 5.5, 6.0, 6.5, 7.0, 7.5; preferably 2.0 to 5.0.

In an embodiment, no more than 10% of the Ge atoms in the molecular sieve SCM-14 are replaced by atoms of at least one element other than silicon and germanium. Preferably, the element other than silicon and germanium is at least one selected from the group consisting of boron, aluminum, tin, zirconium and titanium, preferably at least one selected from the group consisting of boron and titanium.

In an embodiment, the molecular sieve SCM-14 has an X-ray diffraction pattern substantially as shown in Table A-1 or Table A-2 below.

TABLE A-1

| 2θ (°) [a] | d-spacing (Å) [b] | Relative intensity ($I/I_0 \times 100$) |
|---|---|---|
| 6.632 | 13.317 | s-vs |
| 8.384 | 10.537 | s-vs |
| 15.587 | 5.680 | w-m |
| 20.661 | 4.295 | w |
| 21.692 | 4.094 | w-vs |
| 25.693 | 3.464 | w-m |

[a] = ±0.3°,
[b] varies with 2θ.

TABLE A-2

| 2θ (°) [a] | d-spacing (Å) | Relative intensity ($I/I_0 \times 100$) |
|---|---|---|
| 6.632 | 13.344 ± 0.603 | s-vs |
| 8.384 | 10.551 ± 0.377 | s-vs |
| 15.587 | 5.682 ± 0.109 | w-m |
| 20.661 | 4.296 ± 0.062 | w |
| 21.692 | 4.094 ± 0.056 | w-vs |
| 25.693 | 3.465 ± 0.040 | w-m |

[a] = ±0.3°.

According to an aspect of the present application, the X-ray diffraction pattern may further comprise X-ray diffraction peaks substantially as shown in Table B-1 or Table B-2 below.

TABLE B-1

| 2θ (°) [a] | d-spacing (Å) [b] | Relative intensity ($I/I_0 \times 100$) |
|---|---|---|
| 10.289 | 8.591 | w |
| 11.677 | 7.572 | w |
| 13.287 | 6.658 | w |
| 26.231 | 3.395 | w |

[a] = ±0.3°,
[b] varies with 2θ.

TABLE B-2

| 2θ (°) [a] | d-spacing (Å) | Relative intensity ($I/I_0 \times 100$) |
|---|---|---|
| 10.289 | 8.598 ± 0.250 | w |
| 11.677 | 7.577 ± 0.194 | w |
| 13.287 | 6.661 ± 0.150 | w |
| 26.231 | 3.395 ± 0.038 | w |

[a] = ±0.3°.

According to an aspect of the present application, the X-ray diffraction pattern optionally further comprises X-ray diffraction peaks substantially as shown in the following Table,

| 2θ (°) [a] | d-spacing (Å) | Relative intensity ($I/I_0 \times 100$) |
|---|---|---|
| 14.397 | 6.150 ± 0.127 | w |
| 23.479 | 3.786 ± 0.048 | w |
| 23.798 | 3.736 ± 0.046 | w |
| 24.421 | 3.642 ± 0.044 | w |

[a] = ±0.3°.

According to the present application, the mass ratio of the molecular sieve catalyst used in the step (2) to the biomass starting material used in the step (1) is between 0.1 and 5, preferably between 0.2 and 3.

According to the present application, ethylene is charged to the reaction system in step (2) at an ethylene pressure of 0.5 to 5 MPa, preferably 1 to 4M Pa.

According to the present application, the reaction conditions in step (2) include: a reaction temperature of 160-340° C., preferably 200-300° C.; a reaction time of 6-64 h, preferably 12-48 h.

According to the present application, the product obtained in step (2) can be separated to obtain paraxylene by using a conventional method, such as rectification separation and the like.

The present application thus provides a first series of exemplary embodiments as follows:

1. A method for preparing paraxylene, comprising reacting 2,5-dimethylfuran and/or 2,5-hexanedione as a starting material with ethylene in the presence of organic solvent, using M-AlPO and/or SCM-14 molecular sieve as catalyst, to obtain paraxylene.

2. The method according to exemplary embodiment 1 of the first series, wherein M in the M-AlPO molecular sieve is a metal that is at least one selected from the group consisting of Co, Mg, and Zn, and the AlPO molecular sieve is at least one selected from the group consisting of AlPO-17, AlPO-5, AlPO-8, AlPO-11 or AlPO-18, preferably at least one of AlPO-17 and AlPO-5 molecular sieves.

3. The method according to exemplary embodiment 1 or 2 of the first series, wherein the metal content of the M-AlPO molecular sieve is not less than 0.2 wt %, preferably 0.2 wt % to 2.0 wt %.

4. The method according to exemplary embodiment 1 or 2 of the first series, wherein the M-AlPO molecular sieve has a schematic chemical composition represented by the formula "$mP_2O_5 \cdot nAl_2O_3 \cdot pMO_x$", wherein: 0.5≤m/n≤2, and 20≤m/p≤300; preferably 0.8≤m/n≤1.2, 40≤m/p≤200, x being the total number of oxygen atoms required to satisfy the valence of M.

5. The method according to any one of exemplary embodiments 1 to 4 of the first series, wherein the M-AlPO molecular sieve has the following properties: the total acid content is 100-500 $\mu mol \cdot g^{-1}$, preferably 150-400 $\mu mol \cdot g^{-1}$, wherein the weak acid content is not less than 55%, preferably 60%-80%, and the strong acid content is not greater than 35%, preferably 5%-30%.

6. The method according to exemplary embodiment 1 of the first series, wherein the organic solvent comprises one or more of n-hexane, n-heptane, n-octane, tetrahydrofuran, 1,4-dioxane and cyclohexane.

7. The method according to exemplary embodiment 1 of the first series, wherein the mass ratio of the starting material to the catalyst is between 0.5:1 and 20.0:1, preferably between 1.0:1 and 8.0:1.

8. The method according to exemplary embodiment 1 of the first series, wherein the mass ratio of the organic solvent to the starting material is between 5:1 and 50:1, preferably between 10:1 and 20:1.

9. The method according to exemplary embodiment 1 of the first series, wherein the reaction system is charged with ethylene under a pressure of 0.5 to 8M Pa, preferably 1 to 5M Pa.

10. The method according to exemplary embodiment 1 of the first series, wherein the reaction conditions include: a reaction temperature of 160-340° C., preferably 200-300° C.; and/or a reaction time of 6-64 h, preferably 8-48 h.

11. An M-AlPO molecular sieve having a schematic chemical composition represented by the formula $mP_2O_5 \cdot nAl_2O_3 \cdot pMO_x$, wherein: 0.5≤m/n≤2, and 20≤m/p≤300; preferably 0.8≤m/n≤1.2, 40≤m/p≤200, x being the total number of oxygen atoms required to satisfy the valence of M; the total acid content of the M-AlPO molecular sieve is 100-500 $\mu mol \cdot g^{-1}$, preferably 150-400 $\mu mol \cdot g^{-1}$, wherein the weak acid content is not less than 55%, and preferably 60%-80%; the strong acid content is not greater than 35%, preferably 5% to 30%.

12. The molecular sieve according to exemplary embodiment 11 of the first series, wherein in the M-AlPO molecular sieve, M is a metal that is at least one selected from the group consisting of Co, Mg, Zn, and the AlPO molecular sieve is at least one selected from the group consisting of AlPO-17, AlPO-5, AlPO-8, AlPO-11, and AlPO-18, preferably at least one of AlPO-17 and AlPO-5 molecular sieves.

The present application thus provides a second series of exemplary embodiments as follows:

1. A method for preparing biomass-derived toluene from methylfuran, comprising the following steps:

contacting methylfuran with ethylene for reaction in the presence of an optional organic solvent and a catalyst comprising an A-SCM-X molecular sieve, wherein A in the A-SCM-X molecular sieve is at least one selected from the group consisting of Sn, Zr and Ti, and X is 14 or 15.

2. The method of claim 1, wherein:

the catalyst is an A-SCM-X molecular sieve or a molded catalyst of the A-SCM-X molecular sieve, and preferably the catalyst is the A-SCM-X molecular sieve; and/or the conditions of the contact and reaction include:

a reaction temperature of 180-300° C., and preferably 210-270° C.; and/or a reaction time of 4-72 h, preferably 10-50 h; and/or a reaction pressure of 1-8 MPa, preferably 2-5 MPa.

3. The method of claim 1 or 2, wherein:

the contacting is carried out in the presence of an organic solvent that is one or more selected from the group consisting of n-heptane, n-octane, tetrahydrofuran, methyl isobutyl ketone and cyclohexane; and/or the catalyst is an A-SCM-X molecular sieve; and/or the mass ratio of methylfuran to catalyst is 0.2-8:1, preferably 0.5-6:1, and preferably 0.8-2:1; and/or the mass ratio of the organic solvent to methylfuran is 10-80:1, preferably 20-50:1; and/or the ethylene is dilute ethylene, which is charged into the reaction system, the concentration of the dilute ethylene is 10-25 v %, and other gas in the dilute ethylene is inert gas.

4. The method according to any one of claims 1 to 3, wherein:

the content of the component A, calculated as oxides, in the A-SCM-X molecular sieve is not less than 0.5 wt %, preferably 0.8 wt % to 3.5 wt %, and more preferably 1.2 wt % to 3.2 wt %; and/or the Lewis acid content of the A-SCM-X molecular sieve is 30-500 $\mu mol \cdot g^{-1}$, preferably 50-300 $\mu mol \cdot g^{-1}$, and more preferably 83-292 $\mu mol \cdot g^{-1}$.

5. The method of any one of claims 1-4, wherein:

the Lewis/Bronst acid ratio of the A-SCM-X molecular sieve is 0.5-10, preferably 0.6-5, and more preferably 0.6-2.1; and/or the A-SCM-X molecular sieve is Sn-SCM-14, Sn-SCM-15, Zr-SCM-14, Zr-SCM-15, Ti-SCM-14 or Ti-SCM-15 molecular sieve.

6. The method of any one of claims 1-5, wherein:

the A-SCM-X molecular sieve has a schematic chemical composition represented by the formula "$mSiO_2 \cdot nGeO_2 \cdot pAO_2$", wherein: 1≤m/n≤30, preferably 2≤m/n≤10, more preferably 3.5≤m/n≤8.7; 20≤m/p≤200, preferably 30≤m/p≤150, more preferably 30≤m/p≤96;

and/or the A component is located in the framework of the molecular sieve.

7. The method of any one of claims 1 to 6, wherein the method for the preparation of the A-SCM-X molecular sieve comprises:

(1) mixing and contacting an SCM-X molecular sieve with an acid-containing organic solution, and performing pretreatment, washing, drying and calcining to obtain a solid;

(2) mixing the solid with a precursor solution containing an A metal source, drying and calcining.

8. The method of claim 7, wherein:

the SCM-X molecular sieve is an SCM-14 molecular sieve and/or an SCM-15 molecular sieve; and/or in the acid-containing organic solution, the organic solvent is at least one selected from dimethyl sulfoxide, tetrahydrofuran, 1,4-dioxane, methanol and ethanol, and is preferably dimethyl sulfoxide; and/or the acid is selected from organic acid and/or inorganic acid, preferably the acid is at least one selected from the group consisting of oxalic acid, hydrochloric acid, sulfuric acid, nitric acid and acetic acid, preferably hydrochloric acid; and/or in the acid-containing organic solution, the acid concentration is 0.001-1 mol/L, preferably 0.005-0.1 mol/L.

9. The method of claim 7 or 8, wherein:

the solid-liquid mass ratio of the SCM-X molecular sieve to the acid-containing organic solution is 1: 10-40, preferably 1: 15-20; and/or the precursor containing the A metal source is at least one selected from the group consisting of an A-containing organic metal complex, an A-containing metal salt and an A-containing metal hydroxide; and/or the mass ratio of A in the precursor solution containing the A metal source to the SCM-X molecular sieve is 1: 20-200; more preferably 1: 30-83.

10. The method of any one of claims 6 to 8, wherein:

the pretreatment conditions in the step (1) include:

a temperature of 30-100° C., preferably 35-90° C., and more preferably 40-80° C.; and/or a period of 0.25 to 24 hours, preferably 0.5 to 18 hours, and more preferably 0.75 to 12 hours; and/or the calcining conditions in the step (1) and the step (2) respectively include: a calcining temperature of 300-650° C.; and/or a calcining time of 1-12 hours; and/or a calcining atmosphere of oxygen or air.

Compared with the prior art, the present application has the following beneficial effects:

The method of the present application takes biomass as a starting material, which is low in price and wide in source, and no acid catalyst is used in the reaction process, thereby avoiding the problems of equipment corrosion, environmental pollution, high treatment cost and the like caused by the use of acid. In addition, the method is simple in process, can efficiently and selectively promote the conversion of biomass to paraxylene by only two steps of continuous reactions, wherein in the first step, a multiphase system formed by a specific organic solvent, an inorganic salt and water is used, the biomass is subjected to hydrolysis and hydrogenation and then hydrated to form an intermediate product (the yield of HDO can reach 55% or higher), then separated to obtain an organic phase comprising 2,5-hexanedione, which is directly used as the starting material of the second step without separating the 2,5-hexanedione; and in the second step, a specific molecular sieve catalyst is used, the conversion rate of the HDO can reach 90% or higher, and the selectivity of the pX product can reach 95% or higher. Meanwhile, the two types of catalysts selected in the present application are tested for cycling stability, and no significant change in the performance of the catalyst is observed after four cycles, which indicates that the reaction system has high stability.

DETAILED DESCRIPTION OF THE INVENTION

Figure 1:
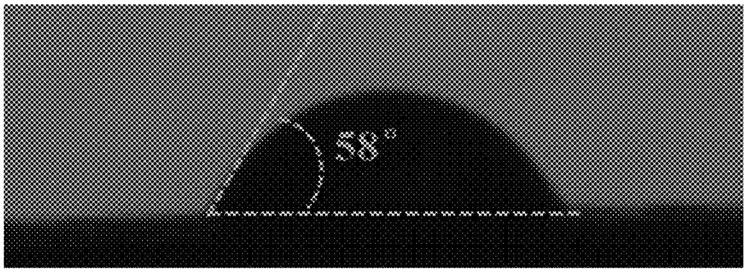
FIG. 1 shows a diagram showing the measurement results of the contact angle of the 5% Pd/C hydrogenation catalyst obtained in Example 1 with water.

In the context of the present application, all technical features and preferred features mentioned herein in relation to the various aspects, series and/or embodiments may be combined with each other to form new technical solutions, unless stated otherwise.

In the context of the present application, unless stated otherwise, the specific steps, specific values and specific materials mentioned in the examples may be combined with other features in other parts of the specification. For example, where the Summary or Detailed Description section of the specification mentions a reaction temperature of 10 to 100° C. and the working examples describe a specific reaction temperature of 20° C., it is to be understood that the range of 10 to 20° C. or the range of 20 to 100° C. has been specifically disclosed herein and may be combined with other features in other sections of the specification to form new embodiments.

In the context of the present application, unless otherwise indicated, the terms “comprising”, “containing”, “including”, “having”, and the like are to be construed as open-ended, but should also be construed to cover closed-ended situations as if all such situations were explicitly set forth herein. For example, the term “comprising” means that other elements not listed may also be comprised, but it should also be construed that the case where only the listed elements are comprised is also explicitly disclosed.

In the context of the present application, unless stated otherwise, the specific steps, specific values and specific materials mentioned in the examples may be combined with other features in other parts of the specification. For example, where the Summary or Detailed Description section of the specification mentions a reaction temperature of 10 to 100° C. and the working examples describe a specific reaction temperature of 20° C., it is to be understood that the range of 10 to 20° C. or the range of 20 to 100° C. has been specifically disclosed herein and may be combined with other features in other sections of the specification to form new embodiments.

In the present application, the $NH_3$ temperature programmed desorption ($NH_3$-TPD) experiment is carried out on a TPD/TPR Altamira AMI-3300 instrument, the total acid content is calculated by fitting and peak separation on the obtained spectrum, the acid corresponding to the desorption temperature of 100-240° C. is defined as weak acid, the acid corresponding to the desorption temperature of 240-320° C. is defined as medium strong acid, and the acid corresponding to the desorption temperature of 320-510° C. is defined as strong acid, so that the proportion of the weak acid and the strong acid is calculated.

In the present application, the XRD measurement method of the molecular sieve product is carried out as follows: the sample is analyzed using a Rigaku Ultima IV X-ray powder diffractometer of RIGAKU, Japan, with a CuKα radiation source (λ=1.54 Å), a nickel filter, 2θ scanning range of 2°-50°, an operating voltage of 35 kV, a current of 25 mA, and a scanning rate of 10°/min.

In the present application, 2,5-hexanedione (HDO), paraxylene pX are analyzed and characterized by gas chromatography-mass spectrometry (GC-MS), and the yield and conversion of 2,5-hexanedione and the yield of reaction product pX are analyzed by Gas Chromatography (GC). The GC-MS instrument is Agilent 7890A of Agilent, U.S.A., of which the chromatographic column is an HP-5 nonpolar capillary column (30 m, 0.53 mm), the gas chromatograph is Agilent 7890B, of which the detector is a hydrogen flame ionization detector (FID), and the chromatographic column is an SE-54 capillary column (30 m, 0.53 mm).

The reaction for producing pX from biomass starting material is divided into two steps, the first step is to prepare 2,5-hexanedione (HDO) from the biomass starting material, and the yield of the intermediate product 2,5-hexanedione is calculated according to the following equation:

Yield of 2,5-hexanedione product, %=(molar amount $n_1$ of 2,5-hexanedione produced by the reaction)/(molar amount no of hexose unit in the reaction substrate biomass)×100%, wherein the hexose unit is $C_6H_{10}O_5$.

In the second step of reaction, the 2,5-hexanedione ($n_1$) generated in the first step is used as a starting material, and reacts with high-pressure ethylene to produce pX, and the conversion of 2,5-hexanedione is calculated according to the following equation:

Conversion of 2,5-hexanedione, %=(molar amount $n_2$ of 2,5-hexanedione remained after the second reaction step)/(molar amount $n_1$ of 2,5-hexanedione in the starting material of the second reaction step)×100%;

In the second step, the yield and selectivity of the product pX are calculated according to the following equations:

Yield of the product pX, %=(molar amount $n_3$ of pX produced by the reaction)/(molar amount $n_1$ of 2,5-hexanedione in the starting material of the second reaction step)×100%.

Selectivity of the product pX, %=(molar amount $n_3$ of pX produced by the reaction)/(molar amount $n_1$ of 2,5-hexanedione in the starting material of the second reaction step−molar amount $n_2$ of 2,5-hexanedione remained after the second reaction step)×100%.

In the present application, the contact angle measuring instrument is DSA100 of KRUSS, Germany. A tangent of the gas-liquid interface is taken from the intersection point of the gas, liquid and solid phases, and the included angle θ between the tangent and the solid-liquid boundary line passing through the contact point of the three phases is the contact angle of the liquid on the solid surface. Where the gas is air, the solid is the hydrogenation catalyst, and the liquid is water, the measured contact angle is defined as the contact angle of the hydrogenation catalyst with water, wherein the larger the contact angle, the better the relative hydrophobicity of the hydrogenation catalyst.

Figure 14:
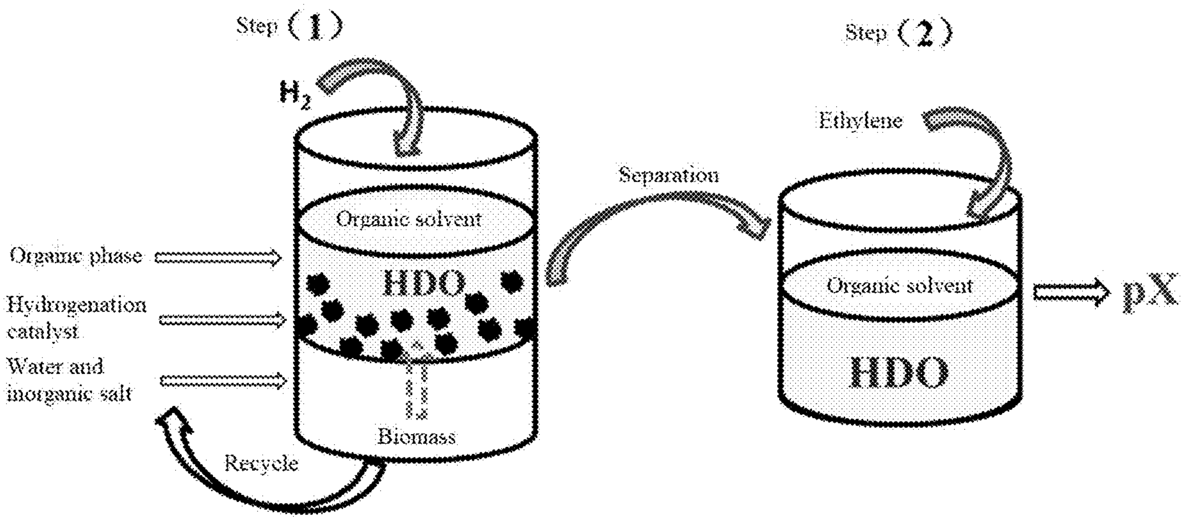
FIG. 14 shows a schematic flow diagram of the production of para-xylene by conversion of biomass according to the present application.

The method for preparing para-xylene by biomass conversion according to the present application is described below with reference to FIG. 14:

(1) contacting a biomass starting material with a hydrogenation catalyst for reaction in a multiphase system formed by an organic solvent, an inorganic salt and water, using hydrogen as a hydrogen source, and subjecting the resulting product to centrifugal separation to obtain an upper organic phase comprising 2,5-hexanedione;

(2) directly contacting the organic phase comprising 2,5-hexanedione obtained in the step (1) with ethylene and an aluminophosphate molecular sieve catalyst for reaction to obtain a reaction product comprising paraxylene. The resulting reaction product comprising paraxylene can be subjected to a subsequent separation process to obtain the paraxylene.

The present application will be described in more detail with reference to the following examples, which are provided to facilitate understanding of the present application and should not be construed as limiting the present application.

Example 1

Firstly, 10 g of activated carbon sample was treated in an oven at 80° C. for 4 h, then the sample was transferred to a high-temperature tube furnace, nitrogen was introduced as carrier gas, the gas flow rate was 3 $h^{-1}$, the temperature was raised to 700° C. at a heating rate of 5° C., and the temperature was kept for 8 h, so that a hydrophobic activated carbon (represented by C) was obtained.

Preparation of catalyst 5% Pd/C: palladium nitrate was impregnated onto the hydrophobic active carbon by an isovolumetric impregnation method, wherein the impregnation amount was determined according to a mass ratio of the noble metal Pd:C of 5:100. The resultant was treated in an oven at 80° C. for 8 h, transferred to a high-temperature tube furnace, nitrogen was introduced as a carrier gas at a gas flow rate of 3 $h^{-1}$, the temperature was raised to 500° C. at a heating rate of 10° C., kept for 4 h, and cooled to room temperature to obtain PdO/C. The carrier gas was switched to hydrogen at a gas flow rate of 3 $h^{-1}$ and the temperature was raised to 400° C. at a heating rate of 10° C., and kept for 4 hours. The carrier gas was switched to nitrogen again and cooled to room temperature to obtain 5% Pd/C. The contact angle measured thereafter was 58°, as shown in FIG. 1, indicating that the material had a good hydrophobicity.

Cellulose was used as a biomass starting material, 5% Pd/C was used as a hydrogenation catalyst, the mass ratio of the biomass starting material to the hydrogenation catalyst was 1, the mass ratio of NaCl to water was 0.5, 1,4-dioxane was used as an organic solvent, the mass ratio of the organic solvent to NaCl and water was 5, the mass ratio of the organic solvent to the biomass starting material was 20, the hydrogen pressure was 2 MPa, the reaction temperature was 200° C., and the reaction time was 10 hours.

The detailed operation was as follows: 0.5 g of cellulose, 0.5 g of 5% Pd/C hydrogenation catalyst, 2 g of NaCl and water (the mass ratio of NaCl to water was 0.5), and 10 g of 1,4-dioxane organic solvent were charged into a high-pressure reactor, and 2 MPa of hydrogen was introduced. The reactor was heated to a preset temperature using a temperature programming heating sleeve, then stirred by magnetic stirring. After 10 hours of reaction at 200° C., the reaction solution was centrifuged to obtain an organic phase comprising 2,5-hexanedione, and the HDO yield was 63%, as calculated based on gas phase analysis.

Example 2

Figure 2:
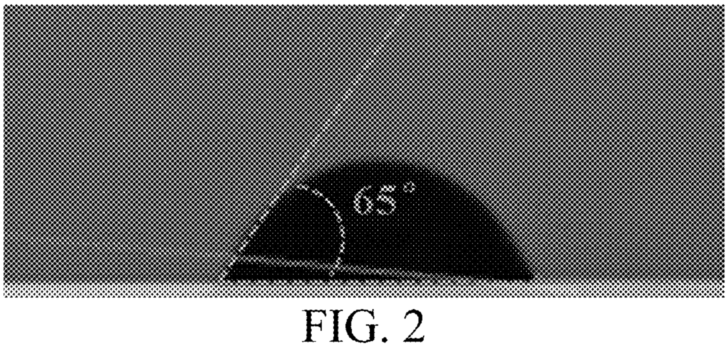
FIG. 2 shows a diagram showing the measurement results of the contact angle of the 5% Pt/Gr hydrogenation catalyst obtained in Example 2 with water.

A catalyst was prepared as described in Example 1, except that graphene was used instead of activated carbon and chloroplatinic acid was used instead of palladium nitrate. The catalyst obtained was 5% Pt/Gr. The contact angle of the catalyst with water was measured to be 65°, as shown in FIG. 2, indicating that the material has a good hydrophobicity.

Glucose was used as a biomass starting material, 5% Pt/Gr was used as a hydrogenation catalyst, the mass ratio of the biomass starting material to the hydrogenation catalyst was 1, the mass ratio of NaCl to water was 0.40, tetrahydrofuran was used as an organic solvent, the mass ratio of the organic solvent to NaCl and water was 8, the mass ratio of the organic solvent to the biomass starting material was 30, the hydrogen pressure was 2.5 MPa, the reaction temperature was 210° C., and the reaction time was 15 hours.

The detailed operation was as follows: 0.5 g of glucose, 0.5 g of 5% Pt/Gr hydrogenation catalyst, 1.9 g of NaCl and water (the mass ratio of NaCl to water was 0.40), and 15 g of tetrahydrofuran organic solvent were charged into a high-pressure reactor, and 2.5 MPa hydrogen was introduced. The reactor was heated to a preset temperature using a temperature programming heating sleeve, then stirred by magnetic stirring. After 15 hours of reaction at 210° C., the reaction solution was centrifuged to obtain an organic phase comprising 2,5-hexanedione, and the HDO yield was 61%, as calculated based on gas phase analysis.

Example 3

A catalyst was prepared as described in Example 1, except that the palladium nitrate was replaced with chloroplatinic acid and the impregnation amount was changed in accordance with a mass ratio of the noble metal Pt:C of 3:100. The catalyst obtained was 3% Pt/C. The contact angle of the catalyst with water was measured to be 63°, similar to that shown in FIG. 1, indicating that the material has a good hydrophobicity.

Fructose was used as a biomass starting material, 3% Pt/C was used as a hydrogenation catalyst, the mass ratio of the biomass starting material to the hydrogenation catalyst was 1.7, the mass ratio of NaCl to water was 0.30, methyl isobutyl ketone was used as an organic solvent, the mass ratio of the organic solvent to NaCl and water was 7, the mass ratio of the organic solvent to the biomass starting material was 18, the hydrogen pressure was 1 MPa, the reaction temperature was 180° C., and the reaction time was 12 hours.

The detailed operation was as follows: 0.5 g of fructose, 0.3 g of 3% Pt/C hydrogenation catalyst, 1.3 g of NaCl and water (the mass ratio of NaCl to water was 0.30), and 9 g of methyl isobutyl ketone organic solvent were charged into a high-pressure reactor, and 1 MPa hydrogen was introduced. The reactor was heated to a preset temperature using a temperature programming heating sleeve, then stirred by magnetic stirring. After 12 hours of reaction at 180° C., the reaction solution was centrifuged to obtain an organic phase comprising 2,5-hexanedione, and the HDO yield was 53%, as calculated based on gas phase analysis.

Example 4

A catalyst was prepared as described in Example 3, except that palladium nitrate was used in place of chloroplatinic acid and graphene was used in place of activated carbon. The catalyst obtained was 3% Pd/Gr. The contact angle of the catalyst with water was measured to be 67°, similar to that shown in FIG. 1, indicating that the material has a good hydrophobicity.

Cellobiose was used as a biomass starting material, 3% Pd/Gr was used as a hydrogenation catalyst, the mass ratio of the biomass starting material to the hydrogenation catalyst was 0.5, the mass ratio of KCl to water was 0.25, γ-valerolactone was used as an organic solvent, the mass ratio of the organic solvent to KCl and water was 5, the mass ratio of the organic solvent to the biomass starting material was 40, the hydrogen pressure was 3 MPa, the reaction temperature was 200° C., and the reaction time was 8 hours.

The detailed operation was as follows: 0.5 g of cellobiose, 1.0 g of 3% Pd/Gr hydrogenation catalyst, 4 g of KCl and water (the mass ratio of KCl to water was 0.25), and 20 g of γ-valerolactone organic solvent were charged into a high-pressure reactor, and 3 MPa hydrogen was introduced. The reactor was heated to a preset temperature using a temperature programming heating sleeve, then stirred by magnetic stirring. After 8 hours of reaction at 200° C., the reaction solution was separated to obtain an organic phase comprising 2,5-hexanedione, and the HDO yield was 54%, as calculated based on gas phase analysis.

Example 5

A 5% Pt/Gr hydrogenation catalyst was prepared as described in Example 2.

Inulin was used as a biomass starting material, 5% Pt/Gr was used as a hydrogenation catalyst, the mass ratio of the biomass starting material to the hydrogenation catalyst was 1.7, the mass ratio of KBr to water was 0.34, 1,2-dichloroethane was used as an organic solvent, the mass ratio of the organic solvent to the KBr and water was 6, the mass ratio of the organic solvent to the biomass starting material was 20, the hydrogen pressure was 1.5 MPa, the reaction temperature was 190° C., and the reaction time was 10 hours.

The detailed operation was as follows: 0.5 g of inulin, 0.3 g of 5% Pt/Gr hydrogenation catalyst, 1.7 g of KBr and water (the mass ratio of the KBr to water was 0.34), 10 g of 1,2-dichloroethane organic solvent were charged into a high-pressure reactor, and 1.5 MPa of hydrogen was introduced. The reactor was heated to a preset temperature using a temperature programming heating sleeve, then stirred by magnetic stirring. After 10 hours of reaction at 190° C., the reaction solution was centrifuged to obtain an organic phase comprising 2,5-hexanedione, and the HDO yield was 58%, as calculated based on gas phase analysis.

Example 6

A 3% Pd/C catalyst was prepared as described in Example 1, except that the impregnation amount was determined in accordance with a mass ratio of the noble metal Pd:C of 3:100. The contact angle of the catalyst with water was measured to be 61°, similar to that shown in FIG. 1, indicating that the material has a good hydrophobicity.

Corn straw was used as a biomass starting material, 3% Pd/C was used as a hydrogenation catalyst, the mass ratio of the biomass starting material to the hydrogenation catalyst was 0.5, the mass ratio of NaCl to water was 0.20, 1,2-dichloroethane was used as an organic solvent, the mass ratio of the organic solvent to NaCl and water was 10, the mass ratio of the organic solvent to the biomass starting material was 30, the hydrogen pressure was 2 MPa, the reaction temperature was 210° C., and the reaction time was 13 hours.

The detailed operation was as follows: 0.5 g of corn straw, 1.0 g of 3% Pd/C hydrogenation catalyst, 1.5 g of NaCl and water (the mass ratio of NaCl to water was 0.20), 15 g of 1,2-dichloroethane organic solvent were charged into a high-pressure reactor, and 2 MPa of hydrogen was introduced. The reactor was heated to a preset temperature using a temperature programming heating sleeve, then stirred by magnetic stirring. After reacting at 210° C. for 13 hours, the reaction solution was centrifuged to obtain an organic phase comprising 2,5-hexanedione, and the HDO yield was 52%, as calculated based on gas phase analysis.

Example 7

A 3% Pd/Gr hydrogenation catalyst was prepared as described in Example 4.

Corncob was used as a biomass starting material, 3% Pd/Gr was used as a hydrogenation catalyst, the mass ratio of the biomass starting material to the hydrogenation catalyst was 0.8, the mass ratio of NaCl to water was 0.65, methyl isobutyl ketone was used as an organic solvent, the mass ratio of the organic solvent to NaCl and water was 8, the mass ratio of the organic solvent to the biomass starting material was 36, the hydrogen pressure was 3 MPa, the reaction temperature was 200° C., and the reaction time was 18 hours.

The detailed operation was as follows: 0.5 g of corncob, 0.6 g of 3% Pd/Gr hydrogenation catalyst, 2.3 g of NaCl and water (the mass ratio of NaCl to water was 0.65), 18 g of methyl isobutyl ketone organic solvent were charged into a high-pressure reactor, and 3 MPa of hydrogen was introduced. The reactor was heated to a preset temperature using a temperature programming heating sleeve, then stirred by magnetic stirring. After reacting at 200° C. for 18 hours, the reaction solution was centrifuged to obtain an organic phase comprising 2,5-hexanedione, and the HDO yield was 65%, as calculated based on gas phase analysis.

Example 8

A 3% Pt/C hydrogenation catalyst was prepared as described in Example 3.

Pine wood was used as a biomass starting material, 3% Pt/C was used as a hydrogenation catalyst, the mass ratio of the biomass starting material to the hydrogenation catalyst was 1.3, the mass ratio of NaCl to water was 0.28, tetrahydrofuran was used as an organic solvent, the mass ratio of the organic solvent to NaCl and water was 10, the mass ratio of the organic solvent to the biomass starting material was 18, the hydrogen pressure was 1 MPa, the reaction temperature was 220° C., and the reaction time was 16 hours.

The detailed operation was as follows: 0.5 g of pine wood, 0.4 g of 3% Pt/C hydrogenation catalyst, 0.9 g of 28 wt % of salinity NaCl and water (the mass ratio of NaCl to water was 0.28) and 9 g of tetrahydrofuran organic solvent were charged into a high-pressure reactor, and 1 MPa of hydrogen was introduced. The reactor was heated to a preset temperature using a temperature programming heating sleeve, then stirred by magnetic stirring. After 16 hours of reaction at 220° C., the reaction solution was centrifuged to obtain an organic phase comprising 2,5-hexanedione, and the HDO yield was 55%, as calculated based on gas phase analysis.

Example 9

A 3% Pd/Gr hydrogenation catalyst was prepared as described in Example 4.

Poplar wood was used as a biomass starting material, 3% Pd/Gr was used as a hydrogenation catalyst, the mass ratio of the biomass starting material to the hydrogenation catalyst was 1, the mass ratio of NaCl to water was 0.30, methyl isobutyl ketone was used as an organic solvent, the mass ratio of the organic solvent to NaCl and water was 5, the mass ratio of the organic solvent to the biomass starting material was 20, the hydrogen pressure was 2 MPa, the reaction temperature was 190° C., and the reaction time was 14 hours.

The detailed operation was as follows: 0.5 g of poplar wood, 0.5 g of 3% Pd/Gr hydrogenation catalyst, 2 g of 30 wt % salinity NaCl, water (the mass ratio of NaCl to water was 0.30) and 10 g of methyl isobutyl ketone organic solvent were charged into a high-pressure reactor, and 2 MPa of hydrogen was introduced. The reactor was heated to a preset temperature using a temperature programming heating sleeve, then stirred by magnetic stirring. After 14 hours of reaction at 190° C., the reaction solution was centrifuged to obtain an organic phase comprising 2,5-hexanedione, and the HDO yield was 56%, as calculated based on gas phase analysis.

Example 10

A 5% Pd/C hydrogenation catalyst was prepared as described in Example 1.

Beech wood was used as a biomass starting material, 5% Pd/C was used as a hydrogenation catalyst, the mass ratio of the biomass starting material to the hydrogenation catalyst was 0.7, the mass ratio of NaCl to water was 0.54, tetrahydrofuran was used as an organic solvent, the mass ratio of the organic solvent to NaCl and water was 6, the mass ratio of the organic solvent to the biomass starting material was 30, the hydrogen pressure was 1.5 MPa, the reaction temperature was 200° C., and the reaction time was 8 hours.

The detailed operation was as follows: 0.5 g of beech wood, 0.7 g of 5% Pd/C hydrogenation catalyst, 2.5 g of NaCl and water (the mass ratio of NaCl to water was 0.54), and 15 g of tetrahydrofuran organic solvent were charged into a high-pressure reactor, and 1.5 MPa of hydrogen was introduced. The reactor was heated to a preset temperature using a temperature programming heating sleeve, then stirred by magnetic stirring. After 8 hours of reaction at 200° C., the reaction solution was centrifuged to obtain an organic phase comprising 2,5-hexanedione, and the HDO yield was 64%, as calculated based on gas phase analysis.

To more intuitively describe the reaction conditions and results of Examples 1 to 10 above, the operation parameters and reaction results are listed in Table 1.

TABLE 1

Reaction conditions and results for Examples 1-10

| x. | Biomass starting material | Hydro-genation catalyst | Mass ratio of biomass starting material to hydrogenation catalyst | Mass ratio of organic solvent to biomass starting material | Mass ratio of inorganic salt to water | Organic solvent | Mass ratio of organic solvent to inorganic salt to water | Hydrogen pressure (MPa) | Reaction temperature (° C.) | Reaction time (h) | Yield of HDO (%) |
|---|---|---|---|---|---|---|---|---|---|---|---|
| 1 | Cellulose | 5% Pd/C | 1 | 20 | 0.50 | 1,4-dioxane | 5 | 2 | 200 | 10 | 63 |
| 2 | Glucose | 5% Pt/Gr | 1 | 30 | 0.40 | Tetrahydrofuran | 8 | 2.5 | 210 | 15 | 61 |
| 3 | Fructose | 3% Pt/C | 1.7 | 18 | 0.30 | Methyl isobutyl ketone | 7 | 1 | 180 | 12 | 53 |
| 4 | Cellobiose | 3% Pd/Gr | 0.5 | 40 | 0.25 | γ-valerolactone | 5 | 3 | 200 | 8 | 54 |
| 5 | Inulin | 5% Pt/Gr | 1.7 | 20 | 0.34 | 1,2-dichloroethane | 6 | 1.5 | 190 | 10 | 58 |
| 6 | Corn straw | 3% Pd/C | 0.5 | 30 | 0.20 | 1,2-dichloroethane | 10 | 2 | 210 | 13 | 52 |
| 7 | Corncob | 3% Pd/Gr | 0.8 | 36 | 0.65 | Methyl isobutyl ketone | 8 | 3 | 200 | 18 | 65 |
| 8 | Pine wood | 3% Pt/C | 1.3 | 18 | 0.28 | Tetrahydrofuran | 10 | 1 | 220 | 16 | 55 |
| 9 | Poplar wood | 3% Pd/Gr | 1 | 20 | 0.30 | Methyl isobutyl ketone | 5 | 2 | 190 | 14 | 56 |
| 10 | Beech wood | 5% Pd/C | 0.7 | 30 | 0.54 | Tetrahydrofuran | 6 | 1.5 | 200 | 8 | 64 |

Example 11

Preparation of Co—AlPO-17 molecular sieve: phosphoric acid, aluminum isopropoxide, cobalt phosphate, cyclohexylamine and deionized water were uniformly mixed at a molar ratio of 1 $P_2O_5$:1 $Al_2O_3$:0.01 COO:1 CHA (cyclohexylamine):50 $H_2O$, to form a gel, then subjected to hydrothermal crystallization at 180° C. for 120 hours, washed, dried, and calcined at 550° C. for 5 hours in the presence of air to obtain the Co—AlPO-17 molecular sieve.

Figure 3:
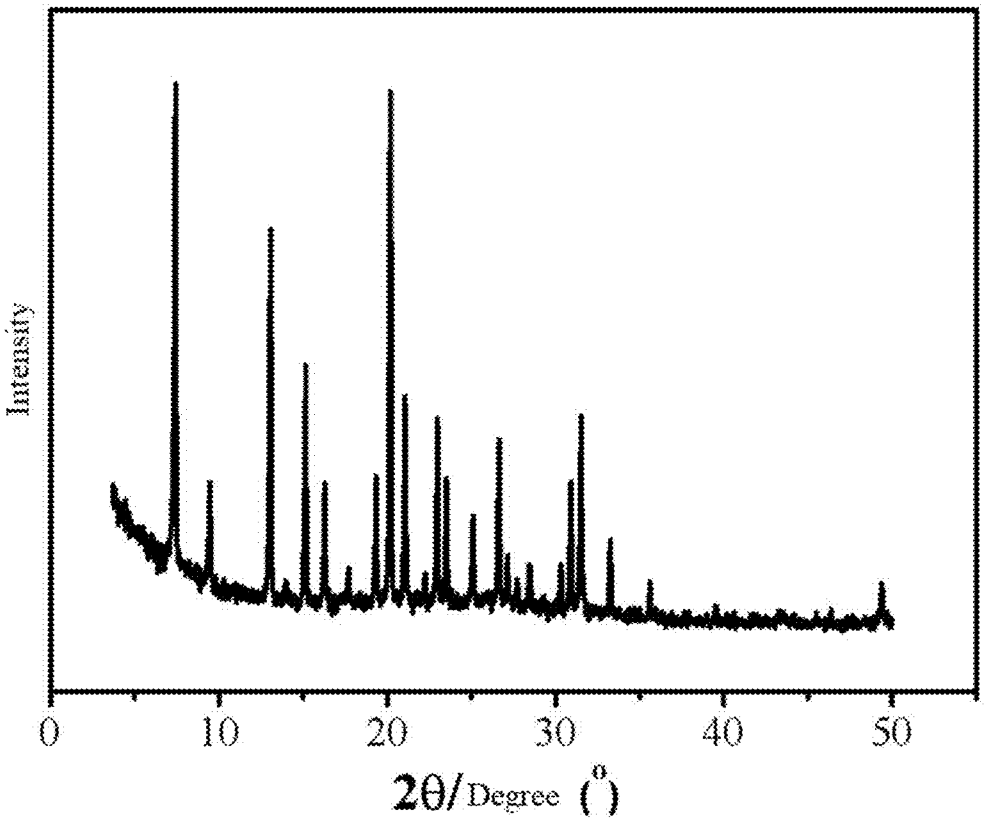
FIG. 3 shows an XRD pattern of the Co—AlPO-17 molecular sieve obtained in Example 11.
Figure 4:
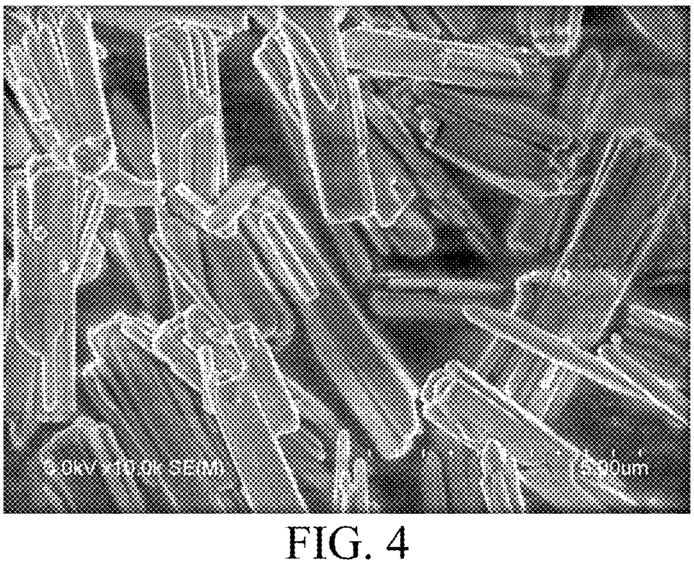
FIG. 4 shows an SEM image of the Co—AlPO-17 molecular sieve obtained in Example 11.
Figure 5:
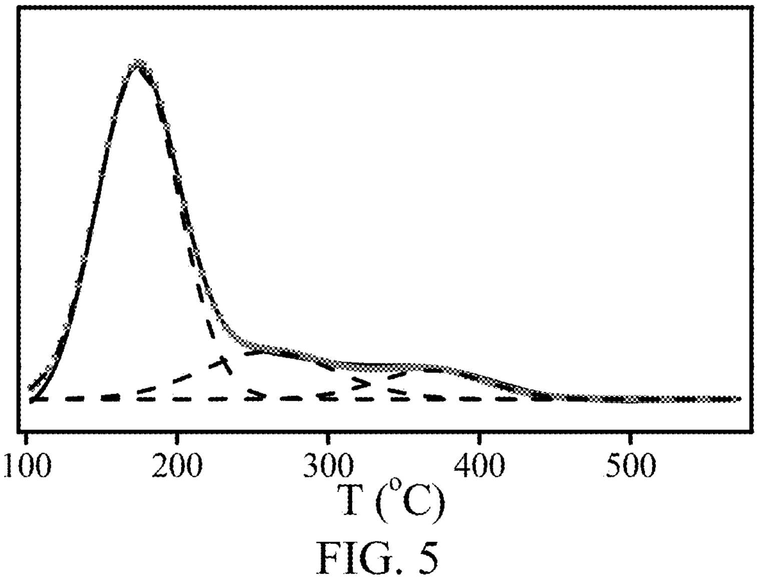
FIG. 5 shows a $NH_3$-TPD diagram of the Co—AlPO-17 molecular sieve obtained in Example 11.

The XRD pattern of the sample is shown in FIG. 3, and its SEM image is shown in FIG. 4. The Co—AlPO-17 molecular sieve has a cobalt content of 0.7 wt % and an exemplary chemical composition of $P_2O_5 \cdot 0.91Al_2O_3 \cdot 0.009CoO$, as measured by inductively coupled plasma atomic emission spectroscopy (ICP). $NH_3$-TPD diagram of the Co—AlPO-17 molecular sieve is shown in FIG. 5, the total acid content is 311 $\mu mol \cdot g^{-1}$, the weak acid content is 72.3%, and the strong acid content is 11.4%.

The organic phase comprising 2,5-hexanedione obtained in Example 1 was used as a starting material, Co—AlPO-17 molecular sieve was used as an aluminophosphate molecular sieve catalyst, the mass ratio of the aluminophosphate molecular sieve catalyst to the biomass starting material used in Example 1 was 1, the ethylene pressure was 3 MPa, the reaction temperature was 260° C., and the reaction time was 30 hours.

The detailed operation was as follows: the organic phase comprising 2,5-hexanedione obtained in Example 1, and 0.5 g of Co—AlPO-17 molecular sieve were charged into a high-pressure reactor, and 3 MPa ethylene was introduced. The reactor was heated to a preset temperature using a temperature programming heating sleeve, then stirred by magnetic stirring. After 30 hours of reaction at 260° C., the reaction solution was centrifuged, and HDO conversion was 92% and pX selectivity was 97%, as calculated based on gas phase analysis.

Example 12

Figure 6:
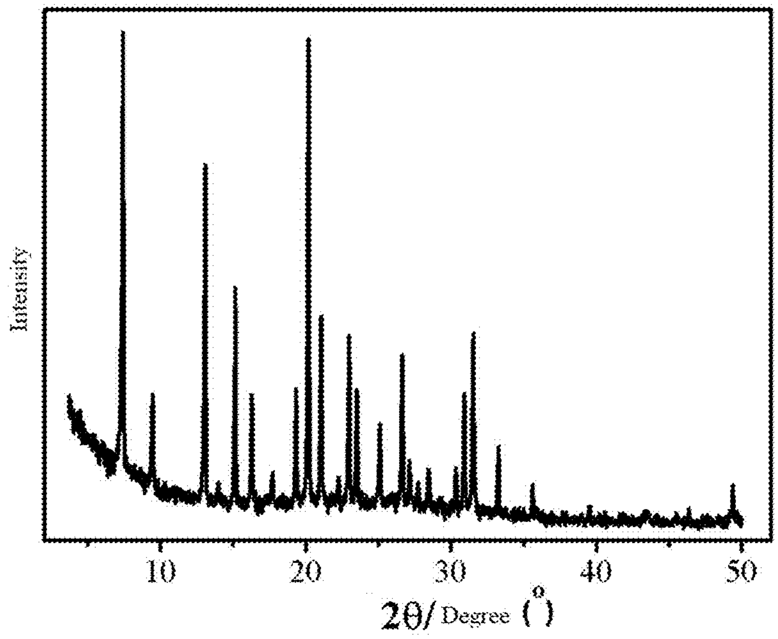
FIG. 6 shows an XRD pattern of the Mg—AlPO-17 molecular sieve obtained in Example 12.
Figure 7:
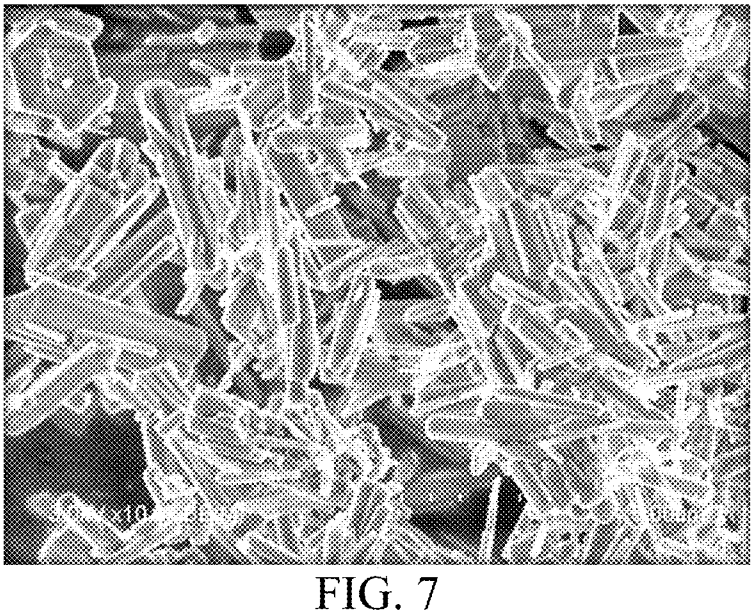
FIG. 7 shows an SEM image of the Mg—AlPO-17 molecular sieve obtained in Example 12.
Figure 8:
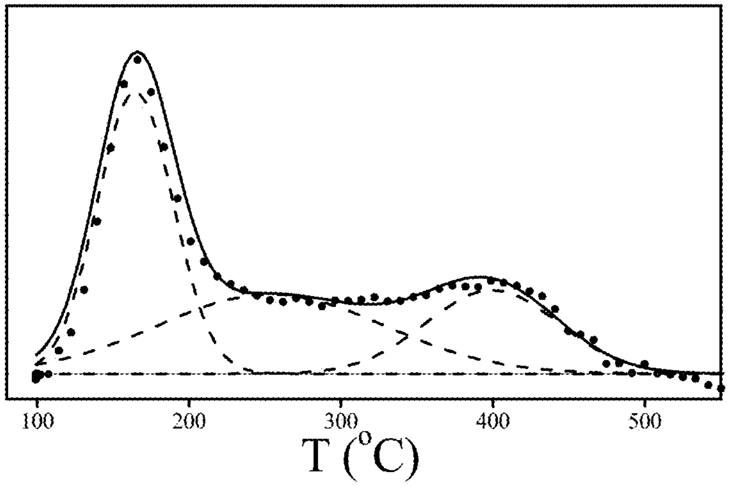
FIG. 8 shows a $NH_3$-TPD diagram of the Mg—AlPO-17 molecular sieve obtained in Example 12.

Preparation of Mg—AlPO-17 molecular sieve: phosphoric acid, aluminum isopropoxide, magnesium nitrate, cyclohexylamine and deionized water were uniformly mixed, at a molar ratio of 1 $P_2O_5$:1.2 $Al_2O_3$:0.02 MgO:1 CHA (cyclohexylamine):50 $H_2O$, to form a gel, then subjected to hydrothermal crystallization at 200° C. for 70 hours, washed, dried, and calcined at 550° C. for 5 hours in the presence of oxygen to obtain the Mg—AlPO-17 molecular sieve. The XRD pattern of the Mg—AlPO-17 molecular sieve is shown in FIG. 6, and its SEM image is shown in FIG. 7. The Mg—AlPO-17 molecular sieve has an Mg content of 1.0 wt % and a schematic chemical composition of $P_2O_5 \cdot 1.12Al_2O_3 \cdot 0.015MgO$, as measured by inductively coupled plasma atomic emission spectroscopy (ICP). $NH_3$-TPD diagram of the Mg—AlPO-17 molecular sieve is shown in FIG. 8, the total acid content is 325 $\mu mol \cdot g^{-1}$, the weak acid content is 67.2%, and the strong acid content is 19.5%.

The organic phase comprising 2,5-hexanedione obtained in Example 1 was used as a starting material, the Mg—AlPO-17 molecular sieve was used as an aluminophosphate molecular sieve catalyst, the mass ratio of the aluminophosphate molecular sieve catalyst to the biomass starting material used in Example 1 was 0.6, the ethylene pressure was 2.5 MPa, the reaction temperature was 230° C., and the reaction time was 36 hours.

The detailed operation was as follows: the organic phase comprising 2,5-hexanedione obtained in Example 1, and 0.3 g of Mg—AlPO-17 molecular sieve were charged into a high-pressure reactor, and 2.5 MPa of ethylene was introduced. The reactor was heated to a preset temperature using a temperature programming heating sleeve, then stirred by magnetic stirring. After 36 hours of reaction at 230° C., the reaction solution was centrifuged, and the HDO conversion was 96% and the pX selectivity was 96%, as calculated based on gas phase analysis.

Example 13

A Mg—AlPO-17 molecular sieve was prepared as described in Example 12.

The organic phase comprising 2,5-hexanedione obtained in Example 3 was used as a starting material, the Mg—AlPO-17 molecular sieve was used as an aluminophosphate molecular sieve catalyst, the mass ratio of the aluminophosphate molecular sieve catalyst to the biomass starting material used in Example 3 was 1.5, the ethylene pressure was 3 MPa, the reaction temperature was 270° C., and the reaction time was 24 hours.

The detailed operation was as follows: the organic phase comprising 2,5-hexanedione obtained in Example 3, and 0.75 g of Mg—AlPO-17 molecular sieve were charged into a high-pressure reactor and 3 MPa of ethylene was introduced. The reactor was heated to a preset temperature using a temperature programming heating sleeve, then stirred by magnetic stirring. After 24 hours of reaction at 270° C., the reaction solution was centrifuged, and HDO conversion was 90% and pX selectivity was 97%, as calculated based on gas phase analysis.

Example 14

Figure 9:
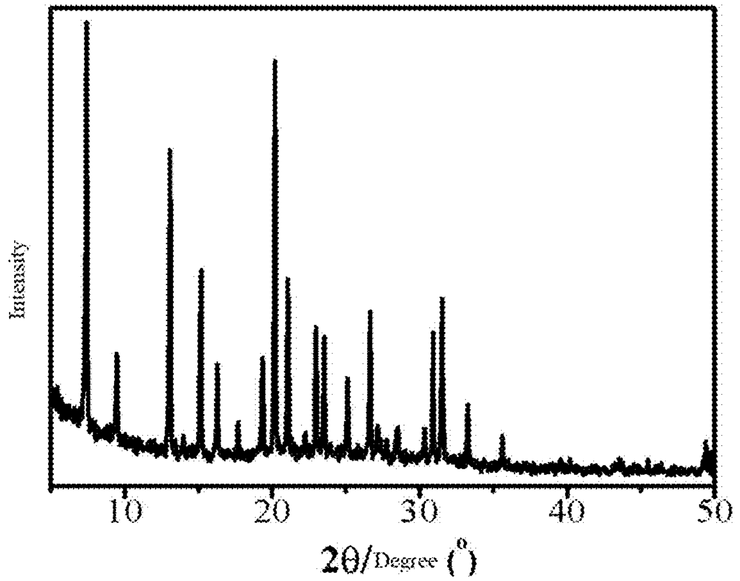
FIG. 9 shows an XRD pattern of the Zn—AlPO-17 molecular sieve obtained in Example 14.

Preparation of Zn—AlPO-17 molecular sieve: phosphoric acid, aluminum isopropoxide, zinc nitrate, cyclohexylamine and deionized water were uniformly mixed, at a molar ratio of 1 $P_2O_5$:1.1 $Al_2O_3$:0.01 ZnO:1 CHA (cyclohexylamine): 50 $H_2O$, to form a gel, subjected to hydrothermal crystallization for 96 hours at 200° C., washed, dried, and calcined for 5 hours at 550° C. in the presence of oxygen to obtain the Zn—AlPO-17 molecular sieve. The SEM image of the sample is similar to that shown in FIG. 4 and shows a rod-like shape; the XRD pattern of the Zn—AlPO-17 molecular sieve is shown in FIG. 9. The Zn—AlPO-17 molecular sieve has a zinc content of 0.7 wt % and a schematic chemical composition of $P_2O_5 \cdot 1.03Al_2O_3 \cdot 0.008ZnO$, as measured by inductively coupled plasma atomic emission spectroscopy (ICP). $NH_3$-TPD diagram of the sample is similar to that shown in FIG. 5, the total acid content is 254 $\mu mol \cdot g^{-1}$, the weak acid content is 71.2% and the strong acid content is 12.1%.

The organic phase comprising 2,5-hexanedione obtained in Example 4 was used as a starting material, the Zn—AlPO-17 molecular sieve was used as an aluminophosphate molecular sieve catalyst, the mass ratio of the aluminophosphate molecular sieve catalyst to the biomass starting material used in Example 4 was 2, the ethylene pressure was 3.5 MPa, the reaction temperature was 240° C., and the reaction time was 40 hours.

The detailed operation was as follows: the organic phase comprising 2,5-hexanedione obtained in Example 4, and 1 g Zn—AlPO-17 molecular sieve were charged into a high-pressure reactor, and 3.5 MPa ethylene was introduced. The reactor was heated to a preset temperature using a temperature programming heating sleeve, then stirred by magnetic stirring. After 40 hours of reaction at 240° C., the reaction solution was centrifuged, and the HDO conversion was 95% and the pX selectivity was 95%, as calculated based on gas phase analysis.

Example 15

A Zn—AlPO-17 molecular sieve was prepared as described in Example 14.

The organic phase comprising 2,5-hexanedione obtained in Example 5 was used as a starting material, the Zn—AlPO-17 molecular sieve was used as an aluminophosphate molecular sieve catalyst, the mass ratio of the aluminophosphate molecular sieve catalyst to the biomass starting material used in Example 5 was 0.8, the ethylene pressure was 1.8 MPa, the reaction temperature was 250° C., and the reaction time was 48 hours.

The detailed operation was as follows: the organic phase comprising 2,5-hexanedione obtained in Example 5, and 0.4 g of Zn—AlPO-17 molecular sieve were charged into a high-pressure reactor, and 1.8 MPa of ethylene was introduced. The reactor was heated to a preset temperature using a temperature programming heating sleeve, then stirred by magnetic stirring. After 48 hours of reaction at 250° C., the reaction solution was centrifuged, and the HDO conversion was 99% and the pX selectivity was 98%, as calculated based on gas phase analysis.

Example 16

A Co—AlPO-17 molecular sieve was prepared as described in Example 11.

The organic phase comprising 2,5-hexanedione obtained in Example 6 was used as a starting material, the Co—AlPO-17 molecular sieve was used as an aluminophosphate molecular sieve catalyst, the mass ratio of the aluminophosphate molecular sieve catalyst to the biomass starting material used in Example 6 was 1.4, the ethylene pressure was 2 MPa, the reaction temperature was 250° C., and the reaction time was 32 hours.

The detailed operation was as follows: the organic phase comprising 2,5-hexanedione obtained in Example 6, and 0.7 g of Co—AlPO-17 molecular sieve were charged into a high-pressure reactor, and 2 MPa ethylene was introduced. The reactor was heated to a preset temperature using a temperature programming heating sleeve, then stirred by magnetic stirring. After reacting at 250° C. for 32 hours, the reaction solution was centrifuged, and the HDO conversion was 95% and the pX selectivity was 96%, as calculated based on gas phase analysis.

Example 17

A Co—AlPO-17 molecular sieve was prepared as described in Example 11.

The organic phase comprising 2,5-hexanedione obtained in Example 7 was used as a starting material, the Co—AlPO-17 molecular sieve was used as an aluminophosphate molecular sieve catalyst, the mass ratio of the aluminophosphate molecular sieve catalyst to the biomass starting material used in Example 7 was 1.6, the ethylene pressure was 1.5 MPa, the reaction temperature was 230° C., and the reaction time was 24 hours.

The detailed operation was as follows: the organic phase comprising 2,5-hexanedione obtained in Example 7, and 0.8 g of Co—AlPO-17 molecular sieve were charged into a high-pressure reactor, and 1.5 MPa of ethylene was introduced. The reactor was heated to a preset temperature using a temperature programming heating sleeve, then stirred by magnetic stirring. After 24 hours of reaction at 230° C., the reaction solution was centrifuged, and the HDO conversion was 91% and the pX selectivity was 98%, as calculated based on gas phase analysis.

Example 18

A Mg—AlPO-17 molecular sieve was prepared as described in Example 12.

The organic phase comprising 2,5-hexanedione obtained in Example 9 was used as a starting material, the Mg—AlPO-17 molecular sieve was used as an aluminophosphate molecular sieve catalyst, the mass ratio of the aluminophosphate molecular sieve catalyst to the biomass starting material used in Example 9 was 2.5, the ethylene pressure was 3 MPa, the reaction temperature was 260° C., and the reaction time was 28 hours.

The detailed operation was as follows: the organic phase comprising 2,5-hexanedione obtained in Example 9, and 1.25 g of Mg—AlPO-17 molecular sieve were charged into a high-pressure reactor and 3 MPa of ethylene was introduced. The reactor was heated to a preset temperature using a temperature programming heating sleeve, then stirred by magnetic stirring. After reacting at 260° C. for 28 hours, the reaction solution was centrifuged, and the HDO conversion was 94% and the pX selectivity was 97%, as calculated based on gas phase analysis.

Example 19

Figure 10:
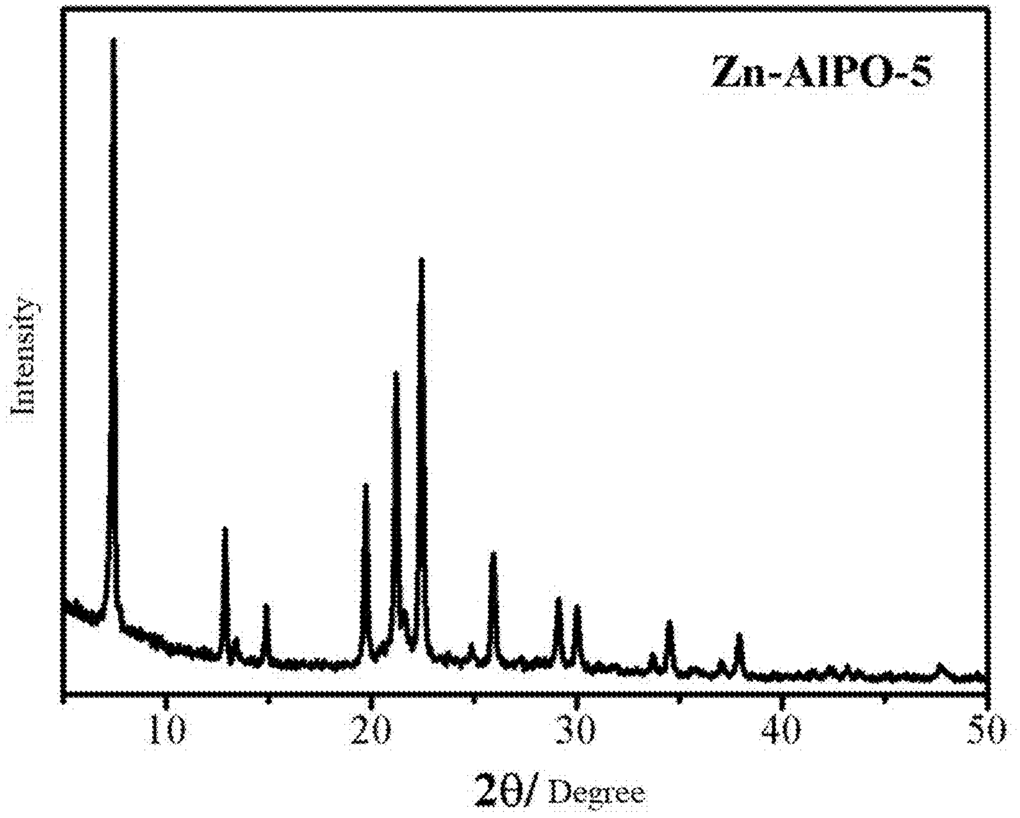
FIG. 10 shows an XRD pattern of the Zn—AlPO-5 molecular sieve obtained in Example 19.

Preparation of Zn—AlPO-5 molecular sieve: phosphoric acid, aluminum isopropoxide, zinc nitrate, ethylenediamine and deionized water were uniformly mixed, at a molar ratio of according to 1.0 $P_2O_5$:1.0 $Al_2O_3$:0.01 ZnO:1.0 ethylene diamine:50 $H_2O$, to form a gel, then subjected to hydrothermal crystallization for 4 hours at 190° C., washed, dried, and calcined for 5 hours at 550° C. in the presence of oxygen to obtain the Zn—AlPO-5 molecular sieve. The SEM image of the sample is similar to that shown in FIG. 4, and shows a rod-like shape; the XRD pattern of the sample is shown in FIG. 10. The sample has a zinc content of 0.7 wt % and a schematic chemical composition of $P_2O_5 \cdot 0.92Al_2O_3 \cdot 0.009ZnO$, as measured by inductively coupled plasma atomic emission spectroscopy (ICP). $NH_3$-TPD diagram of the sample is similar to that shown in FIG. 3, the total acid content is 235 $\mu mol \cdot g^{-1}$, the weak acid content is 67.3% and the strong acid content is 16.5%.

The organic phase comprising 2,5-hexanedione obtained in Example 1 was used as a starting material, the Zn—AlPO-5 molecular sieve was used as an aluminophosphate molecular sieve catalyst, the mass ratio of the aluminophosphate molecular sieve catalyst to the biomass starting material used in Example 1 was 1, the ethylene pressure was 2 MPa, the reaction temperature was 260° C., and the reaction time was 26 hours.

The detailed operation was as follows: the organic phase comprising 2,5-hexanedione obtained in Example 1, and 0.5 g of Zn—AlPO-5 molecular sieve were charged into a high-pressure reactor, and 2 MPa of ethylene was introduced. The reactor was heated to a preset temperature using a temperature programming heating sleeve, then stirred by magnetic stirring. After reaction at 260° C. for 26 hours, the reaction solution was centrifuged, and the HDO conversion was 91% and the pX selectivity was 96%, as calculated based on gas phase analysis.

To more intuitively describe the reaction conditions and results of Examples 11-19 above, the operation parameters and results are listed in Table 2.

Example 20

In this example, the SCM-14 molecular sieve obtained in Example 1 of CN109081360B was used as a catalyst.

The organic phase comprising 2,5-hexanedione obtained in Example 9 was used as a starting material, the SCM-14 molecular sieve was used as a catalyst, the mass ratio of the catalyst to the biomass starting material used in Example 9 was 2.5, the ethylene pressure was 3 MPa, the reaction temperature was 250° C., and the reaction time was 24 hours.

The detailed operation was as follows: the organic phase comprising 2,5-hexanedione obtained in Example 9, and 1.25 g of SCM-14 molecular sieve were charged into a high-pressure reactor, and 3 MPa of ethylene was introduced. The reactor was heated to a preset temperature using a temperature programming heating sleeve, then stirred by magnetic stirring. After 24 hours of reaction at 250° C., the reaction solution was centrifuged, and the HDO conversion was 91% and the pX selectivity was 96%, as calculated based on gas phase analysis.

Example 21

Figure 11:
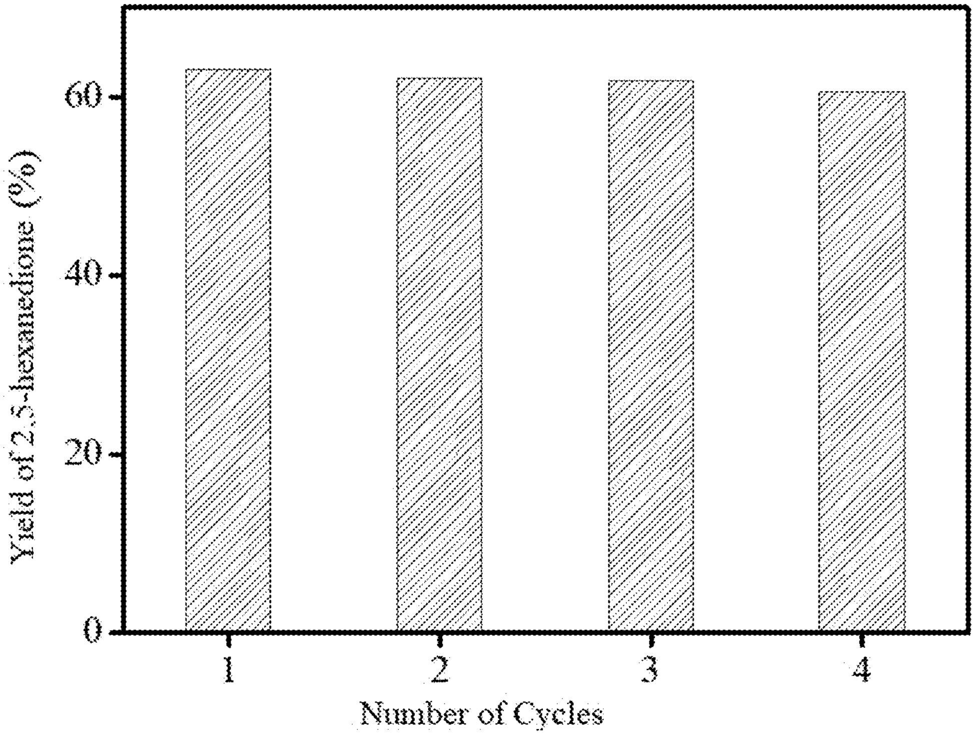
FIG. 11 shows a diagram showing the cycle results of Example 21 in which 5% Pt/Gr was used to catalyze the production of HDO from glucose.

The operation procedures of the cycling stability experiment were as follows: to NaCl and water obtained after the completion of the reaction in Example 2 and the 5% Pt/Gr catalyst in Example 2, 0.5 g of glucose and 15 g of tetrahydrofuran were added directly to conduct a new reaction, and 2.5 MPa of hydrogen was introduced. The reactor was heated to a preset temperature using a temperature programming heating sleeve, then stirred by magnetic stirring. After 15 hours of reaction at 210° C., the reaction solution was centrifuged to obtain an organic phase comprising 2,5-hexanedione, and the HDO yield was calculated based on gas phase analysis. Total 4 cycles of reactions were conducted in this way, and the HDO yield remained above 60% after 4 cycles of reactions as shown in FIG. 11, indicating that the hydrogenation catalyst added in the reaction system in the first reaction step had good cycling stability.

Example 22

The organic phases comprising 2,5-hexanedione obtained in the cycling test of Example 21 were used as a starting material, and the organic phases were used in the order obtained in the cycling test, the Co—AlPO-17 molecular

TABLE 2

Reaction conditions and results for Examples 11-19

| Examples | Source of HDO | Aluminophosphate molecular sieve catalyst | Mass ratio of aluminophosphate molecular sieve catalyst to biomass starting material | Ethylene pressure (MPa) | Reaction temperature (° C.) | Reaction time (h) | HDO conversion (%) | pX selectivity (%) |
|---|---|---|---|---|---|---|---|---|
| 11 | Example 1 | Co—AlPO-17 | 1 | 3 | 260 | 30 | 92 | 97 |
| 12 | Example 1 | Mg—AlPO-17 | 0.6 | 2.5 | 230 | 36 | 96 | 96 |
| 13 | Example 3 | Mg—AlPO-17 | 1.5 | 3 | 270 | 24 | 90 | 97 |
| 14 | Example 4 | Zn—AlPO-17 | 2 | 3.5 | 240 | 40 | 95 | 95 |
| 15 | Example 5 | Zn—AlPO-17 | 0.8 | 1.8 | 250 | 48 | 99 | 98 |
| 16 | Example 6 | Co—AlPO-17 | 1.4 | 2 | 250 | 32 | 95 | 96 |
| 17 | Example 7 | Co—AlPO-17 | 1.6 | 1.5 | 230 | 24 | 91 | 98 |
| 18 | Example 9 | Mg—AlPO-17 | 2.5 | 3 | 260 | 28 | 94 | 97 |
| 19 | Example 1 | Zn—AlPO-5 | 1 | 2 | 260 | 26 | 91 | 96 |

sieve obtained in Example 11 was used as an aluminophosphate molecular sieve catalyst, the mass ratio of the aluminophosphate molecular sieve catalyst to the biomass starting material used in Example 20 was 1, the ethylene pressure was 3 MPa, the reaction temperature was 260° C., and the reaction time was 30 hours.

Figure 12:
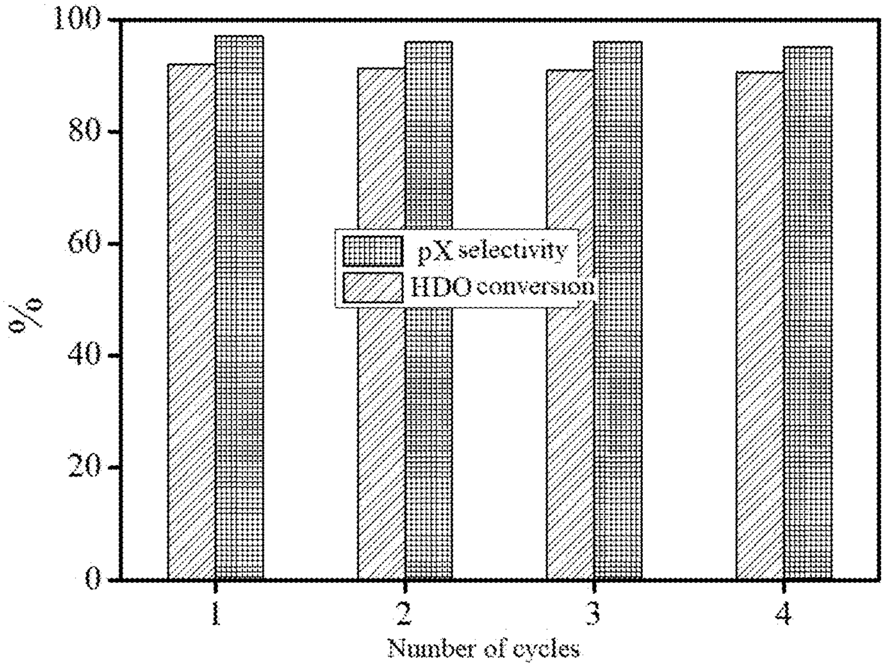
FIG. 12 shows a diagram showing the cycle results of Example 22 in which a Co—AlPO-17 molecular sieve is used to catalyze the production of pX from HDO.

The detailed operation was as follows: the organic phase comprising 2,5-hexanedione obtained in each cycle of Example 20 and 0.5 g of Co—AlPO-17 molecular sieve were charged into a high-pressure reactor, and 3 MPa ethylene was introduced. The reactor was heated to a preset temperature using a temperature programming heating sleeve, then stirred by magnetic stirring. After 30 hours of reaction at 260° C., the reaction solution was separated, and the HDO conversion and pX selectivity were calculated based on gas phase analysis. After the completing of each reaction, the Co—AlPO-17 molecular sieve was separated, and was directly used for the next reaction after being ultrasonically washed with tetrahydrofuran solution, and 4 cycles of reaction were conducted. The results are shown in FIG. 12. The HDO conversion remained above 90% and the pX selectivity remained above 95% after 4 cycles of reactions, indicating that the M-AlPO molecular sieve catalyst used in the reaction system in the second step had good cycling stability.

Comparative Example 1

A 3% Pd/Gr hydrogenation catalyst was prepared as described in Example 4.

Cellobiose was used as a biomass starting material, 3% Pd/Gr was used as a hydrogenation catalyst, the mass ratio of the biomass starting material to the hydrogenation catalyst was 0.5, deionized water was used as aqueous phase, γ-valerolactone was used as an organic solvent, the mass ratio of the organic solvent to water was 5, the mass ratio of the organic solvent to the biomass starting material was 40, the hydrogen pressure was 3 MPa, the reaction temperature was 200° C., and the reaction time was 8 hours.

The detailed operation was as follows: 0.5 g of cellobiose, 1.0 g of 3% Pd/Gr hydrogenation catalyst, 4 g of deionized water and 20 g of γ-valerolactone organic solvent were charged into a high-pressure reactor, and 3 MPa hydrogen was introduced. The reactor was heated to a preset temperature using a temperature programming heating sleeve, then stirred by magnetic stirring. After 8 hours of reaction at 200° C., the reaction solution was separated and the HDO yield was only 7%, as calculated based on gas phase analysis.

Comparative Example 2

Figure 13:
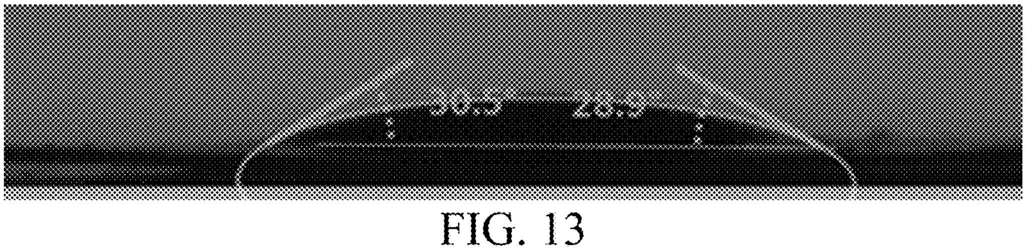
FIG. 13 shows a diagram showing the measurement results of the contact angle of the catalyst obtained in Comparative Example 2 with water.

Preparation of catalyst 5% Pd/DC: palladium nitrate was impregnated on untreated activated carbon (expressed as DC) of Example 1 in an isovolumetric impregnation method at a mass ratio of the noble metal Pd:DC of 5:100. The resultant was treated in an oven at 80° C. for 8 h, transferred to a high-temperature tube furnace, nitrogen was introduced as a carrier gas at a gas flow rate of 3 $h^{-1}$, the temperature was raised to 500° C. at a heating rate of 10° C., kept for 4 h, and cooled to room temperature. The carrier gas was switched to hydrogen at a gas flow rate of 3 $h^{-1}$ and the temperature was raised to 400° C. at a heating rate of 10° C., and kept for 4 hours. The carrier gas was switched to nitrogen again and cooled to room temperature to obtain 5% Pd/DC. Contact angle was then measured to be about 30°, as shown in FIG. 13, indicating that the material had a poor hydrophobicity.

Cellulose was used as a biomass starting material, 5% Pd/DC was used as a hydrogenation catalyst, the mass ratio of the biomass starting material to the hydrogenation catalyst was 1, the mass ratio of NaCl to water was 0.5, 1,4-dioxane was used as an organic solvent, the mass ratio of the organic solvent to NaCl and water was 5, the mass ratio of the organic solvent to the biomass starting material was 20, the hydrogen pressure was 2 MPa, the reaction temperature was 200° C., and the reaction time was 10 hours.

The detailed operation was as follows: 0.5 g of cellulose, 0.5 g of 5% Pd/DC hydrogenation catalyst, 2 g of NaCl and water (the mass ratio of NaCl to water was 0.5), and 10 g of 1,4-dioxane organic solvent were charged into a high-pressure reactor, and 2 MPa of hydrogen was introduced. The reactor was heated to a preset temperature using a temperature programming heating sleeve, then stirred by magnetic stirring. After 10 hours of reaction at 200° C., the reaction solution was centrifuged to obtain an organic phase comprising 2,5-hexanedione, and the HDO yield was only 37%, as calculated based on gas phase analysis.

In the following examples of Series II, the procedure for producing SCM-14 molecular sieve in accordance with the method described in Example 1 of CN109081360A was as follows:

10.08 g of deionized water, 3.045 g of organic template 4-pyrrolidinylpyridine (98 wt %), 1.674 g of germanium oxide (99 wt %), 1.0 g of hydrofluoric acid (40 wt %) and 6.0 g of silica sol ($SiO_2$, 40 wt %) were uniformly mixed to obtain a reaction mixture, wherein the material ratio (molar ratio) of the reaction mixture was as follows: $SiO_2/GeO_2$=2.5; template/$SiO_2$=0.50; $H_2O/SiO_2$=20; after being mixed evenly, the mixture was put into a stainless steel reaction kettle, aged for 4 hours in water bath at a temperature of 80° C., then crystallized for 2 days at a temperature of 100° C. under stirring, and further crystallized for 5 days at a temperature of 170° C. After crystallization was completed, the resultant was filtered, washed and dried for 8 hours at 150° C., to obtain a molecular sieve precursor with a schematic chemical composition of $0.21F\cdot0.06Q\cdot SiO_2\cdot 1/3.7GeO_2\cdot0.02H_2O$. The precursor was calcined in air at 550° C. for 6 hours to obtain the SCM-14 molecular sieve.

In the following examples, the procedure for producing SCM-14 molecular sieve in accordance with the method described in Example 2 of CN109081360A was as follows: the starting materials were fed as described in Example 1 of CN109081360A, and the material ratio (molar ratio) of the reaction mixture was changed as follows: $SiO_2/GeO_2$=3; template/$SiO_2$=0.30; $F/SiO_2$=0.30; $H_2O/SiO_2$=18; after being mixed evenly, the mixture was put into a stainless steel reaction kettle, aged for 1 hour in water bath at a temperature of 80° C., then crystallized for 1 day at a temperature of 110° C. under stirring, and further crystallized for 4 days at a temperature of 165° C. to obtain the SCM-14 molecular sieve.

In the following examples, the procedure for producing SCM-15 molecular sieve in accordance with the method described in Example 1 of CN109081359A was as follows:

43.2 g of deionized water, 42.63 g of organic template 4-pyrrolidinylpyridine (98 wt %), 8.37 g of germanium oxide (99 wt %), 14.0 g of hydrofluoric acid (40 wt %), and 60.0 g of silica sol ($SiO_2$, 40 wt %) were mixed uniformly to obtain a reaction mixture, wherein the material ratio (molar ratio) of the reaction mixture was: $SiO_2/GeO_2$=5; template/$SiO_2$=0.70; $F/SiO_2$=0.70; $H_2O/SiO_2$=12; after being mixed evenly, the mixture was put into a stainless steel reaction kettle, aged for 2 hours in water bath at a temperature of 80° C., and then crystallized for 5 days at a temperature of 170° C. under stirring. After the crystallization was completed, the resultant was filtered, washed and dried at 120° C. for 12 hours to obtain the SCM-15 molecular sieve.

Example II-1

An SCM-14 molecular sieve was synthesized in accordance with the method described in Example 1 of CN109081360A, and added to a dimethyl sulfoxide solution with a concentration of 0.01 mol/L hydrochloric acid (hydrochloric acid concentration of 30 wt %), with a solid-liquid mass ratio of 1:20, and the mixture was pretreated for 3 hours under stirring in a water bath at 60° C. The product was centrifuged and washed till the resulting solution had a pH of 7, dried overnight at 110° C., and then Sn-containing organometallic precursor $(CH_3)_2SnCl_2$ was added, the mass ratio of Sn (the theoretical amount of Sn in the organometallic precursor) to SCM-14 molecular sieve was 1:49, and the mixture was ground thoroughly in a mortar to obtain a uniformly dispersed mixture.

Figure 15:
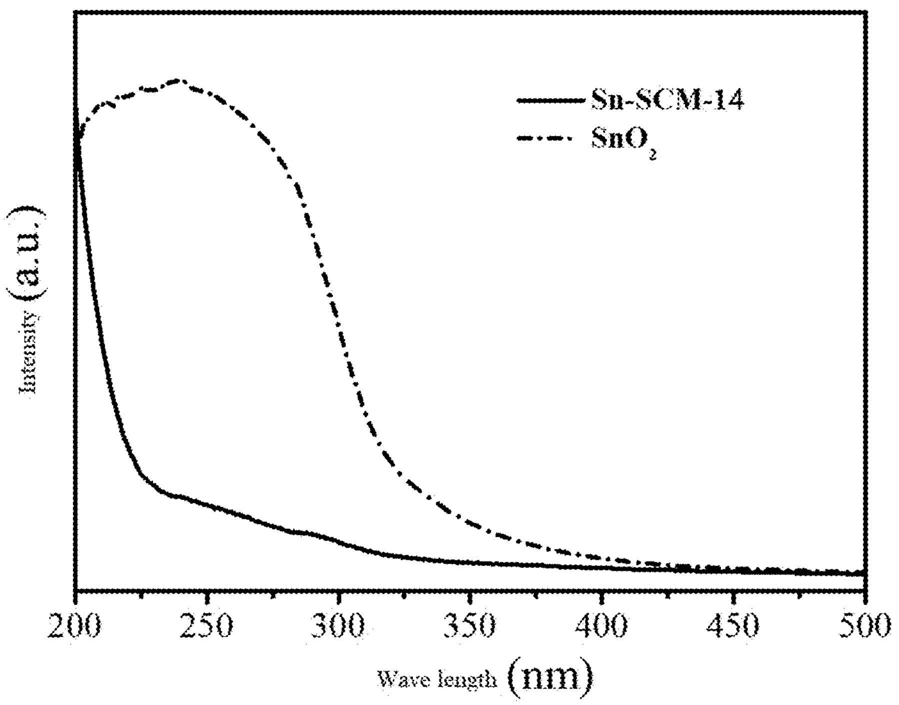
FIG. 15 shows a ultraviolet-visible absorption spectrum (UV-Vis) of the Sn-SCM-14 molecular sieve obtained in Example II-1.
Figure 16:
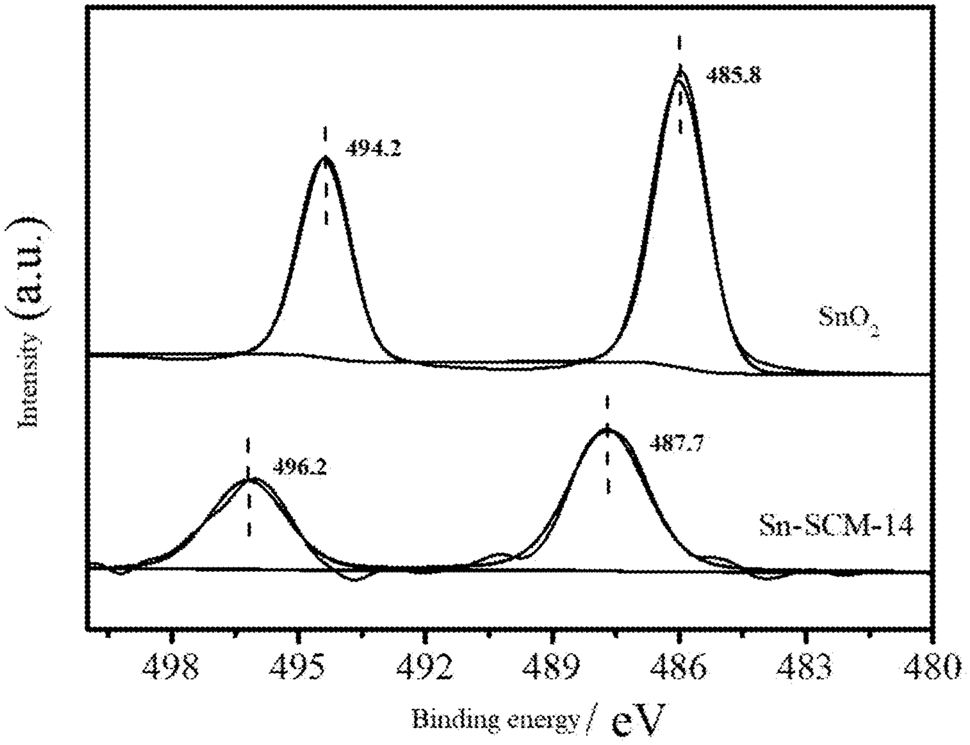
FIG. 16 shows an X-ray photoelectron spectrum (XPS) of the Sn—SCM-14 molecular sieve obtained in Example II-1.
Figure 17:
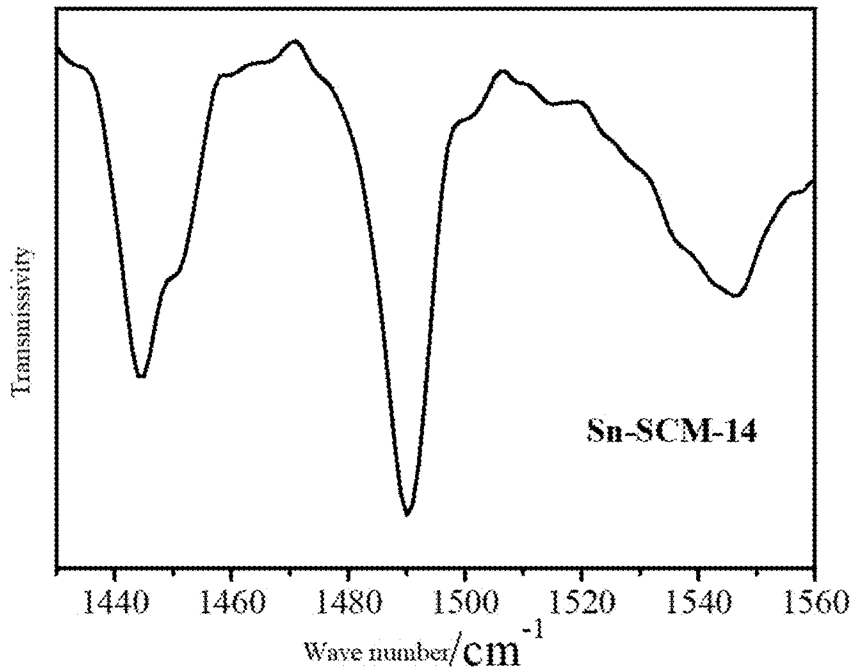
FIG. 17 shows a pyridine adsorption infrared (Py-FTIR) diagram of the Sn—SCM-14 molecular sieve obtained in Example II-1.
Figure 18:
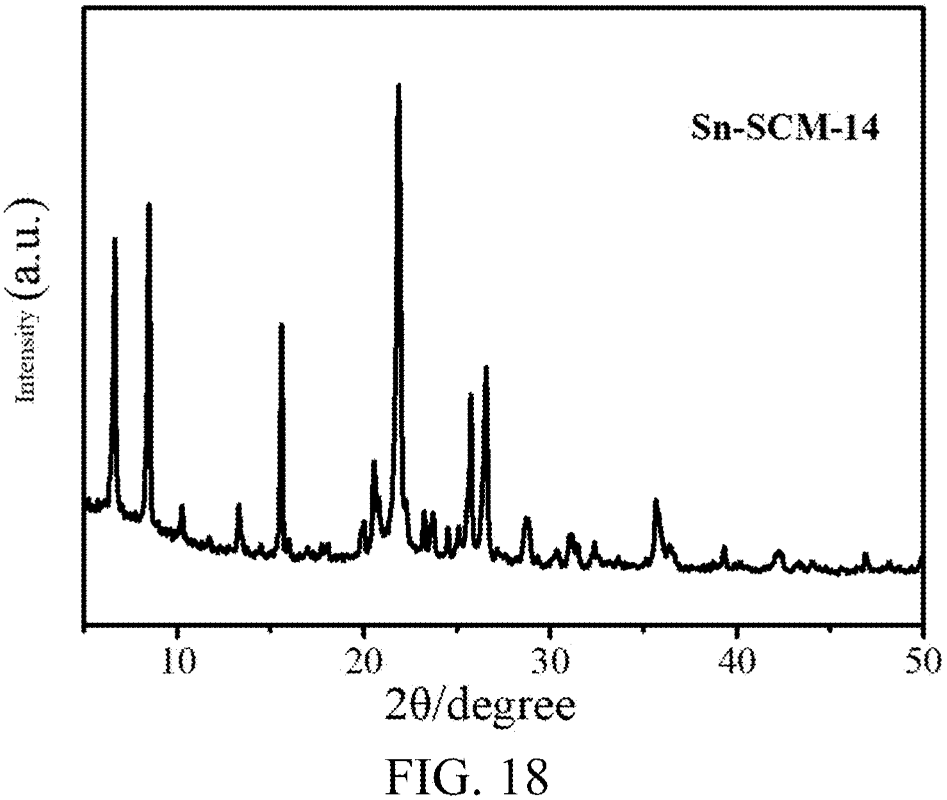
FIG. 18 shows an XRD pattern of the Sn—SCM-14 molecular sieve obtained in Example II-1.

The product was dried in a drying oven at 110° C., and then calcined at 550° C. in air atmosphere for 5 hours to obtain an Sn—SCM-14 molecular sieve, of which the Uv-vis spectrum is shown in FIG. 15, which shows that heteroatom tin species is present in the molecular sieve framework in a four-coordination form, and the XPS spectrum is shown in FIG. 16, which indicates that Sn has successfully entered the framework of the SCM-14 molecular sieve; the pyridine desorption infrared diagram of the sample is shown in FIG. 17, and it can be seen from FIG. 17 that the molecular sieve has two acidic species, i.e. Bronst and Lewis acids. The sample has an atomic ratio Si/Ge=5.2 and an atomic ratio of Si/Sn=57, as measured by inductively coupled plasma atomic emission spectroscopy (ICP). The Lewis acid content is 210 $\mu mol\cdot g^{-1}$, and the ratio of Lewis/Bronst acid is 0.8, as calculated based on the pyridine desorption infrared diagramand, and the content of tin is 2.0 wt %, calculated as oxide. The XRD pattern of the resulted Sn—SCM-14 molecular sieve is shown in FIG. 18, and the uniform dispersion of tin species in the molecular sieve can be seen from FIG. 18.

Example II-2

An SCM-14 molecular sieve was synthesized in accordance with the method described in Example 1 of CN109081360A, and added to a dimethyl sulfoxide solution with a concentration of 0.02 mol/L hydrochloric acid (hydrochloric acid concentration of 30 wt %), with a solid-liquid mass ratio of 1:20, and the mixture was pretreated for 1 hour under stirring in a water bath at 70° C. The product was centrifuged and washed till the resulting solution had a pH of 7, dried overnight at 110° C., and then Sn-containing organometallic precursor $(CH_3)_2SnCl_2$ was added, the mass ratio of Sn (the theoretical amount of Sn in the organometallic precursor) to SCM-14 molecular sieve was 1:33, and the mixture was ground thoroughly in a mortar to obtain a uniformly dispersed mixture.

The product was dried in a drying oven at 110° C., and then calcined at 550° C. for 5 hours to obtain an Sn—SCM-14 molecular sieve, of which the Uv-vis spectrum is similar to that shown in FIG. 15, and the XPS spectrum is similar to that shown in FIG. 16, which indicates that Sn has successfully entered the framework of the SCM-14 molecular sieve; the pyridine desorption infrared diagram of the sample is similar to that shown in FIG. 17. The sample has a ratio of Si/Ge=6.1 (atomic ratio) and a ratio of Si/Sn=39 (atomic ratio), as measured by inductively coupled plasma atomic emission spectroscopy (ICP). The Lewis acid content is 284 $\mu mol\cdot g^{-1}$, and the Lewis/Bronst acid ratio is 1.0, as calculated based on the pyridine desorption infrared diagram, and the content of tin is 2.9 wt %, calculated as oxide.

Example II-3

An SCM-14 molecular sieve was synthesized in accordance with the method described in Example 1 of CN109081360A, the SCM-14 molecular sieve was added into a dimethyl sulfoxide solution with a concentration of 0.01 mol/L nitric acid, the solid-liquid mass ratio was 1:15, and the mixture was pretreated for 2 hours under stirring in a water bath at 40° C. The product was centrifuged and washed till the resulting solution had a pH of 7, dried overnight at 110° C., and then Sn-containing organometallic precursor $(CH_3)_2SnCl_2$ was added, the mass ratio of Sn (the theoretical amount of Sn in the organometallic precursor) to SCM-14 molecular sieve was 1:83, and the mixture was ground thoroughly in a mortar to obtain a uniformly dispersed mixture.

The product was dried in a drying oven at 110° C., and then calcined at 550° C. for 5 hours to obtain an Sn—SCM-14 molecular sieve, of which the Uv-vis spectrum is similar to that shown in FIG. 15, and the XPS spectrum is similar to that shown in FIG. 16, which indicates that Sn has successfully entered the framework of the SCM-14 molecular sieve; the pyridine desorption infrared diagram of the sample is similar to that shown in FIG. 17. The sample has a ratio of Si/Ge=5.4 (atomic ratio) and a ratio of Si/Sn=96 (atomic ratio), as measured by inductively coupled plasma atomic emission spectroscopy (ICP). The Lewis acid content is 124 $\mu mol\cdot g^{-1}$, the ratio of Lewis/Bronst acid is 0.6, as calculated based on the pyridine desorption infrared diagram, and the content of tin is 1.2 wt %, calculated as oxide.

Example II-4

An SCM-14 molecular sieve was synthesized in accordance with the method described in Example 2 of CN109081360A, the SCM-14 molecular sieve was added into a dimethyl sulfoxide solution with a concentration of 0.008 mol/L oxalic acid, the solid-liquid mass ratio was 1:15, and the mixture was pretreated for 5 hours under stirring in a water bath at 60° C. The product was centrifuged and washed till the resulting solution had a pH of 7, dried overnight at 110° C., and then Sn-containing organometallic precursor $(CH_3)_2SnCl_2$ was added, the mass ratio of Sn (the theoretical amount of Sn in the organometallic precursor) to SCM-14 molecular sieve was 1:49, and the mixture was ground thoroughly in a mortar to obtain a uniformly dispersed mixture.

The product was dried in a drying oven at 110° C., and then calcined at 550° C. for 5 hours to obtain an Sn—SCM-14 molecular sieve, of which the Uv-vis spectrum is similar to that shown in FIG. 15, and the XPS spectrum is similar to that shown in FIG. 16, which indicates that Sn has successfully entered the framework of the SCM-14 molecular sieve; the pyridine desorption infrared diagram of the sample is similar to that shown in FIG. 17. The sample has a ratio of Si/Ge=3.5 (atomic ratio) and a ratio of Si/Sn=61 (atomic ratio), as measured by inductively coupled plasma atomic emission spectroscopy (ICP). The Lewis acid content is 187 $\mu mol\cdot g^{-1}$, and the ratio of Lewis/Bronst acid is 0.8, as calculated based on the pyridine desorption infrared diagram, and the content of tin is 2.0 wt %, calculated as oxide.

Example II-5

An SCM-14 molecular sieve was synthesized in accordance with the method described in Example 2 of CN109081360A, the SCM-14 molecular sieve was added into a dimethyl sulfoxide solution with a concentration of 0.02 mol/L oxalic acid, the solid-liquid mass ratio was 1:20, and the mixture was pretreated for 3 hours under stirring in a water bath at 70° C. The product was centrifuged and washed till the resulting solution had a pH of 7, dried overnight at 110° C., and then Sn-containing organometallic precursor $(CH_3)_2SnCl_2$ was added, the mass ratio of Sn (the theoretical amount of Sn in the organometallic precursor) to SCM-14 molecular sieve was 1:60, and the mixture was ground thoroughly in a mortar to obtain a uniformly dispersed mixture.

The product was dried in a drying oven at 110° C., and then calcined at 550° C. for 5 hours to obtain an Sn—SCM-14 molecular sieve, of which the Uv-vis spectrum is similar to that shown in FIG. 15, and the XPS spectrum is similar to that shown in FIG. 16, which indicates that Sn has successfully entered the framework of the SCM-14 molecular sieve; the pyridine desorption infrared diagram of the sample is similar to that shown in FIG. 17. The sample has a ratio of Si/Ge=7.4 (atomic ratio) and a ratio of Si/Sn=85 (atomic ratio), as measured by inductively coupled plasma atomic emission spectroscopy (ICP). The Lewis acid content is 153 $\mu mol \cdot g^{-1}$, and the ratio of Lewis/Bronst acid is 0.7, as calculated based on the pyridine desorption infrared diagram, and the content of tin is 1.6 wt %, calculated as oxide.

Example II-6

An SCM-14 molecular sieve was synthesized in accordance with the method described in Example 1 of CN109081360A, the SCM-14 molecular sieve was added into a dimethyl sulfoxide solution with a concentration of 0.01 mol/L acetic acid, the solid-liquid mass ratio was 1:20, and the mixture was pretreated for 6 hours under stirring in a water bath at 60° C. The product was centrifuged and washed the resulting solution had a pH of 7, dried overnight at 110° C., then Zr-containing organometallic precursor $Cp_2ZrCl_2$ was added, the mass ratio of Zr (theoretical amount of Zr in the organometallic precursor) to SCM-14 molecular sieve was 1:49, and the mixture was ground thoroughly in a mortar to obtain a uniformly dispersed mixture.

Figure 19:
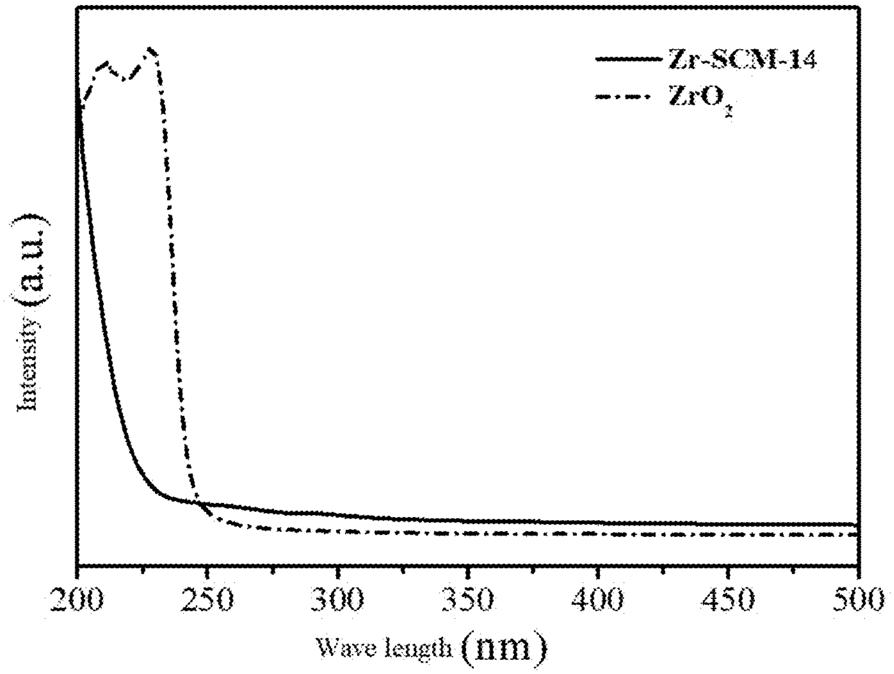
FIG. 19 shows a ultraviolet-visible absorption spectrum (UV-Vis) of the Zr—SCM-14 molecular sieve obtained in Example II-6.
Figure 20:
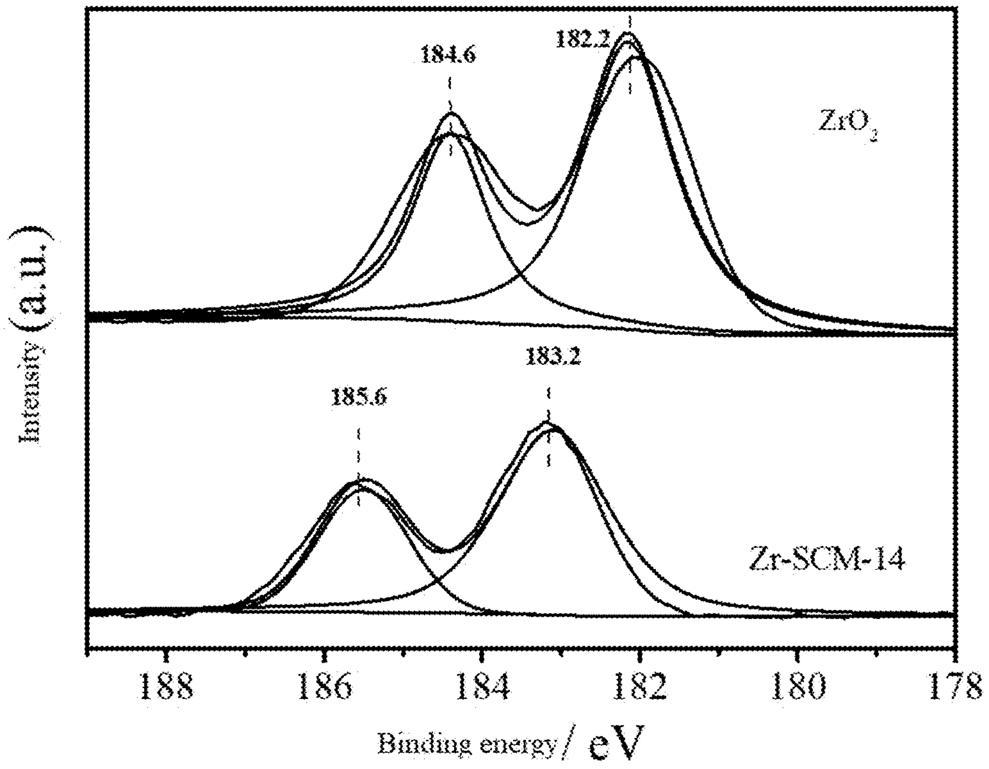
FIG. 20 shows an X-ray photoelectron spectrum (XPS) of the Zr—SCM-14 molecular sieve obtained in Example II-6.

The product was dried in a drying oven at 110° C., and then calcined at 550° C. for 5 hours to obtain the Zr—SCM-14 molecular sieve, wherein the Uv-vis spectrum of the sample is shown in FIG. 19, which shows that the heteroatom zirconium species is present in the molecular sieve framework in a four-coordination form, and its XPS spectrum is shown in FIG. 20, which indicates that Zr has successfully entered the framework of the SCM-14 molecular sieve; the pyridine desorption infrared diagram of the sample is similar to that shown in FIG. 17. The sample has a ratio of Si/Ge=4.3 (atomic ratio) and a ratio of Si/Zr=44 (atomic ratio), as measured by inductively coupled plasma atomic emission spectroscopy (ICP). The Lewis acid content is 237 $\mu mol \cdot g^{-1}$, the ratio of Lewis/Bronst acid is 0.9, as calculated based on the pyridine desorption infrared diagram, and the content of zirconium was 2.0 wt %, calculated as oxide.

Example II-7

An SCM-14 molecular sieve was synthesized in accordance with the method described in Example 2 of CN109081360A, the SCM-14 molecular sieve was added into a dimethyl sulfoxide solution with a concentration of 0.04 mol/L acetic acid, the solid-liquid mass ratio was 1:20, and the mixture was pretreated for 3 hours under stirring in a water bath at 50° C. The product was centrifuged and washed till the resulting solution had a pH of 7, dried overnight at 110° C., then Zr-containing organometallic precursor $Cp_2ZrCl_2$ was added, the mass ratio of Zr (the theoretical amount of Zr in the organometallic precursor) to the SCM-14 molecular sieve was 1:35, and the mixture was ground thoroughly in a mortar to obtain a uniformly dispersed mixture.

The product was dried in a drying oven at 110° C., and then calcined at 550° C. for 5 hours to obtain the Zr—SCM-14 molecular sieve, of which the Uv-vis spectrum is similar to that shown in FIG. 19, and the XPS spectrum is similar to that shown in FIG. 20, which indicates that Zr has successfully entered the framework of the SCM-14 molecular sieve; the pyridine desorption infrared diagram of the sample is similar to that shown in FIG. 17. The sample has a ratio of Si/Ge=7.9 (atomic ratio) and a ratio of Si/Zr=33 (atomic ratio), as measured by inductively coupled plasma atomic emission spectroscopy (ICP). The Lewis acid content was 292 $\mu mol \cdot g^{-1}$, and the ratio of Lewis/Bronst acid is 1.1, as calculated based on the pyridine desorption infrared diagramand, and the content of zirconium was 2.8 wt %, calculated as oxide.

Example II-8

An SCM-15 molecular sieve was synthesized in accordance with the method described in Example 1 of CN109081359A, the SCM-15 molecular sieve was added into a dimethyl sulfoxide solution with a concentration of 0.01 mol/L hydrochloric acid, the solid-liquid mass ratio was 1:15, and the mixture was pretreated for 3 hours under stirring in a water bath at 70° C. The product was centrifuged and washed till the resulting solution had a pH of 7, dried overnight at 110° C., and then Sn-containing organometallic precursor $(CH_3)_2SnCl_2$ was added, the mass ratio of Sn (the theoretical amount of Sn in the organometallic precursor) to SCM-15 molecular sieve was 1:30, and the mixture was ground thoroughly in a mortar to obtain a uniformly dispersed mixture.

The product was dried in a drying oven at 110° C., and then calcined at 550° C. for 5 hours to obtain an Sn—SCM-15 molecular sieve, of which the Uv-vis spectrum is similar to that shown in FIG. 15, and the XPS spectrum is similar to that shown in FIG. 16, which indicates that Sn has successfully entered the framework of the SCM-15 molecular sieve; the pyridine desorption infrared diagram of the sample is similar to that shown in FIG. 17. The sample has a ratio of Si/Ge=8.7 (atomic ratio) and a ratio of Si/Sn=34 (atomic ratio), as measured by inductively coupled plasma atomic emission spectroscopy (ICP). The Lewis acid content was 277 $\mu mol \cdot g^{-1}$, and the ratio of Lewis/Bronst acid is 2.1, as calculated based on the pyridine desorption infrared diagram, and the content of tin is 3.2 wt %, calculated as oxide.

Example II-9

An SCM-15 molecular sieve was synthesized in accordance with the method described in Example 1 of CN109081359A, the SCM-15 molecular sieve was added into a dimethyl sulfoxide solution with a concentration of 0.02 mol/L oxalic acid, the solid-liquid mass ratio was 1:20, and the mixture was pretreated for 2 hours under stirring in a water bath at 80° C. The product was centrifuged and washed till the resulting solution had a pH of 7, dried overnight at 110° C., then Zr-containing organometallic precursor $Cp_2ZrCl_2$ was added, the mass ratio of Zr (the theoretical amount of Zr in the organometallic precursor) to the SCM-15 molecular sieve was 1:30, and the mixture was ground thoroughly in a mortar to obtain a uniformly dispersed mixture.

The product was dried in a drying oven at 110° C., and then calcined at 550° C. for 5 hours to obtain a Zr—SCM-15 molecular sieve, of which the Uv-vis spectrum is similar to that shown in FIG. 19, and the XPS spectrum is similar to that shown in FIG. 20, which indicates that Zr has successfully entered the framework of the SCM-15 molecular sieve; the pyridine desorption infrared diagram of the sample is similar to that shown in FIG. 17. The sample has a ratio of Si/Ge=7.7 (atomic ratio) and a ratio of Si/Zr=30 (atomic ratio), as measured by inductively coupled plasma atomic emission spectroscopy (ICP). The Lewis acid content was 284 μmolog−1, and the ratio of Lewis/Bronst acid is 1.8, as calculated based on the pyridine desorption infrared diagram, and the content of zirconium was 3.1%, calculated as oxide.

Example II-10

An SCM-14 molecular sieve was synthesized in accordance with the method described in Example 1 of CN109081360A, and added to a dimethylsulfoxide solution with a concentration of 0.02 mol/L hydrochloric acid (hydrochloric acid concentration 30 wt %), the solid-liquid mass ratio was 1:20, and the mixture was pretreated for 1 hour under stirring in a water bath at 70° C. The product was centrifuged and washed till the resulting solution had a pH of 7, dried overnight at 110° ° C., and then Sn-containing organometallic precursor $(CH_3)_2SnCl_2$ was added, the mass ratio of Sn (the theoretical amount of Sn in the organometallic precursor) to SCM-14 molecular sieve was 1:160, and the mixture was ground thoroughly in a mortar to obtain a uniformly dispersed mixture.

The product was dried in a drying oven at 110° C., and then calcined at 550° C. for 5 hours to obtain an Sn—SCM-14 molecular sieve, of which the Uv-vis spectrum is similar to that shown in FIG. 15, and the XPS spectrum is similar to that shown in FIG. 16, which indicates that Sn has successfully entered the framework of the SCM-14 molecular sieve; the pyridine desorption infrared diagram of the sample is similar to that shown in FIG. 17. The sample has a ratio of Si/Ge=5.9 (atomic ratio) and a ratio of Si/Sn=190 (atomic ratio), as measured by inductively coupled plasma atomic emission spectroscopy (ICP). The Lewis acid content is 83 $\mu mol \cdot g^{-1}$, the ratio of Lewis/Bronst acid is 0.4, as calculated based on the pyridine desorption infrared diagram, and the content of tin is 0.6 wt %, calculated as oxide.

Examples II-11 to II-20

Methylfuran was used as a substrate and n-heptane was used as a reaction solvent, 1.0 g of the A-SCM-X molecular sieves of Examples II-1 to II-10, 1.0 g of methylfuran, and 30 g of n-heptane were charged into a high-pressure reactor equipped with a stirrer, and 4.0 MPa of dilute ethylene (15 (v) %, the remainder being nitrogen) was introduced. The reactor was heated to a preset temperature using a temperature programming heating sleeve, then stirred by magnetic stirring. The reaction was carried out for 24 hours at a temperature of 260° C., and the reaction solution was analyzed to obtain the conversion rate of methylfuran and the selectivity of the target product toluene, which are shown in Table 1.

TABLE 1

Evaluation results of catalysts of Examples II-1 to II-10

| Example II- | Source of catalyst | Atomic ratio of Si/Ge | Atomic ratio of Si/A (Sn or Zr) | Content of A (wt %) | Lewis acid content (μmol/g) | Ratio of Lewis/Bronst acid | Methylfuran conversion (%) | Toluene Selectivity (%) |
|---|---|---|---|---|---|---|---|---|
| 11 | Example II-1 | 5.2 | 57 | 2.0 | 210 | 0.8 | 90 | 96 |
| 12 | Example II-2 | 6.1 | 39 | 2.9 | 284 | 1.0 | 91 | 95 |
| 13 | Example II-3 | 5.4 | 96 | 1.2 | 104 | 0.6 | 88 | 96 |
| 14 | Example II-4 | 3.5 | 61 | 2.0 | 187 | 0.8 | 90 | 95 |
| 15 | Example II-5 | 7.4 | 85 | 1.6 | 153 | 0.7 | 86 | 94 |
| 16 | Example II-6 | 4.3 | 44 | 2.0 | 237 | 0.9 | 88 | 94 |
| 17 | Example II-7 | 7.9 | 33 | 2.8 | 292 | 1.1 | 93 | 97 |
| 18 | Example II-8 | 8.7 | 34 | 3.2 | 277 | 2.1 | 95 | 95 |
| 19 | Example II-9 | 7.7 | 30 | 3.1 | 284 | 1.8 | 92 | 93 |
| 20 | Example II-10 | 5.9 | 190 | 0.6 | 83 | 0.4 | 80 | 92 |

If the data in the table was inconsistent with the examples, the examples shall control. The same applies below.

Example II-21

In this example, n-heptane was used as a reaction solvent, the mass ratio of n-heptane to methylfuran was 20, the mass ratio of methylfuran to catalyst was 0.8, the reaction temperature was 240° C., and the reaction time was 20 h. 1.0 g of the Sn—SCM-14 molecular sieve of the above Example II-1, 0.8 g of methylfuran and 16 g of n-heptane were charged into a high-pressure reactor equipped with a stirrer, and 2.0 MPa of dilute ethylene (15 (v) %, the remainder being nitrogen) was introduced. The reactor was heated to a preset temperature using a temperature programming heating sleeve, then stirred by magnetic stirring. The reaction was carried out for 20 hours at a temperature of 240° C., and the conversion rate of methylfuran was 91% and the selectivity of toluene was 94%, as calculated based on gas phase analysis of the reaction solution.

Example II-22

In this example, n-heptane was used as a reaction solvent, the mass ratio of n-heptane to methylfuran was 20, the mass ratio of methylfuran to catalyst was 2.0, the reaction temperature was 260° C., and the reaction time was 30 h. 1.0 g of the Sn—SCM-14 molecular sieve of the above Example II-1, 2.0 g of methylfuran and 40 g of n-heptane were charged into a high-pressure reactor equipped with a stirrer, and 5.0 MPa of dilute ethylene (15 (v) %, the remainder being nitrogen) was introduced. The reactor was heated to a preset temperature using a temperature programming heating sleeve, then stirred by magnetic stirring. The reaction was carried out for 30 hours at a temperature of 260° C., and the conversion rate of methylfuran was 87% and the selectivity of toluene was 96%, as calculated based on gas phase analysis of the reaction solution.

Example II-23

In this example, n-octane was used as a reaction solvent, the mass ratio of n-octane to methylfuran was 30, the mass ratio of methylfuran to catalyst was 1.0, the reaction temperature was 250° C., and the reaction time was 18 h. 1.0 g of the Sn—SCM-14 molecular sieve of the above Example II-1, 1.0 g of methylfuran and 30 g of n-octane were charged into a high-pressure reactor equipped with a stirrer, and 4.0 MPa of dilute ethylene (15 (v) %, the remainder being nitrogen) was introduced. The reactor was heated to a preset temperature using a temperature programming heating sleeve, then stirred by magnetic stirring. The reaction was carried out for 18 hours at a temperature of 250° C., and the conversion rate of methylfuran was 89% and the selectivity of toluene was 94%, as calculated based on gas phase analysis of the reaction solution.

Example II-24

In this example, n-octane was used as a reaction solvent, the mass ratio of n-octane to methylfuran was 40, the mass ratio of methylfuran to catalyst was 1.2, the reaction temperature was 240° C., and the reaction time was 25 hours. 1.0 g of the Sn—SCM-14 molecular sieve of the above Example II-1, 1.2 g of methylfuran and 48 g of n-octane were charged into a high-pressure reactor equipped with a stirrer, and 3.0 MPa of dilute ethylene (15 (v) %, the remainder being nitrogen) was introduced. The reactor was heated to a preset temperature using a temperature programming heating sleeve, then stirred by magnetic stirring. The reaction was carried out for 25 hours at a temperature of 240° C., and the conversion rate of methylfuran is 86% and the selectivity of toluene is 95%, as calculated based on gas phase analysis of the reaction solution.

Example II-25

In this example, tetrahydrofuran was used as a reaction solvent, the mass ratio of tetrahydrofuran to methylfuran was 20, the mass ratio of methylfuran to catalyst was 2, the reaction temperature was 260° C., and the reaction time was 24 hours. 1.0 g of the Sn—SCM-14 molecular sieve of the above Example II-1, 2.0 g of methylfuran and 40 g of tetrahydrofuran were charged into a high-pressure reactor equipped with a stirrer, and 3.0 MPa of dilute ethylene (15 (v) %, the remainder being nitrogen) was introduced. The reactor was heated to a preset temperature using a temperature programming heating sleeve, then stirred by magnetic stirring. The reaction was carried out for 24 hours at a temperature of 260° C., and the conversion rate of methylfuran was 90% and the selectivity of toluene was 93%, as calculated based on gas phase analysis of the reaction solution.

Example II-26

In this example, tetrahydrofuran was used as a reaction solvent, the mass ratio of tetrahydrofuran to methylfuran was 25, the mass ratio of methylfuran to catalyst was 1.5, the reaction temperature was 250° C., and the reaction time was 28 hours. 1.0 g of the Sn—SCM-14 molecular sieve of the above Example II-1, 1.5 g of methylfuran and 37.5 g of tetrahydrofuran were charged into a high-pressure reactor equipped with a stirrer, and 2.0 MPa of dilute ethylene (15 (v) %, the remainder being nitrogen) was introduced. The reactor was heated to a preset temperature using a temperature programming heating sleeve, then stirred by magnetic stirring. The reaction was carried out for 28 h at a temperature of 250° C., and the conversion rate of methylfuran was 86% and the selectivity of toluene was 94%, as calculated based on gas phase analysis of the reaction solution.

Example II-27

In this example, methyl isobutyl ketone was used as a reaction solvent, the mass ratio of methyl isobutyl ketone to methylfuran was 20, the mass ratio of methylfuran to catalyst was 3, the reaction temperature was 260° C., and the reaction time was 48 hours. 1.0 g of the Sn—SCM-14 molecular sieve of the above Example II-1, 3.0 g of methylfuran and 60.0 g of methyl isobutyl ketone were charged into a high-pressure reactor equipped with a stirrer, and 5.0 MPa of dilute ethylene (15 (v) %, the remainder being nitrogen) was introduced. The reactor was heated to a preset temperature using a temperature programming heating sleeve, then stirred by magnetic stirring. The reaction was carried out for 48 hours at a temperature of 260° C., and the conversion rate of methylfuran was 85% and the selectivity of toluene was 95%, as calculated based on gas phase analysis of the reaction solution.

Example II-28

In this example, methyl isobutyl ketone was used as a reaction solvent, the mass ratio of methyl isobutyl ketone to methylfuran was 40, the mass ratio of methylfuran to catalyst was 1, the reaction temperature was 250° C., and the reaction time was 20 hours. 1.0 g of the Sn—SCM-14 molecular sieve of the above Example II-1, 1.0 g of methylfuran and 40.0 g of methyl isobutyl ketone were charged into a high-pressure reactor equipped with a stirrer, and 2.0 MPa of dilute ethylene (15 (v) %, the remainder being nitrogen) was introduced. The reactor was heated to a preset temperature using a temperature programming heating sleeve, then stirred by magnetic stirring. The reaction was carried out for 20 hours at a temperature of 250° C., and the conversion rate of methylfuran was 89% and the selectivity of toluene was 94%, as calculated based on gas phase analysis of the reaction solution.

Example II-29

In this example, cyclohexane was used as a reaction solvent, the mass ratio of cyclohexane to methylfuran was 30, the mass ratio of methylfuran to catalyst was 2, the reaction temperature was 260° C., and the reaction time was 30 hours. 1.0 g of the Sn—SCM-14 molecular sieve of the above Example II-1, 2.0 g of methylfuran and 60.0 g of cyclohexane were charged into a high-pressure reactor equipped with a stirrer, and 4.0 MPa of dilute ethylene (15 (v) %, the remainder being nitrogen) was introduced. The reactor was heated to a preset temperature using a temperature programming heating sleeve, then stirred by magnetic stirring. The reaction was carried out for 30 hours at a temperature of 260° C., and the conversion rate of methylfuran was 92% and the selectivity of toluene was 95%, as calculated based on gas phase analysis of the reaction solution.

Example II-30

In this example, cyclohexane was used as a reaction solvent, the mass ratio of cyclohexane to methylfuran was 30, the mass ratio of methylfuran to catalyst was 1.4, the reaction temperature was 250° C., and the reaction time was 48 hours. 1.0 g of the Sn—SCM-14 molecular sieve of the above Example II-1, 1.4 g of methylfuran and 42.0 g of cyclohexane were charged into a high-pressure reactor equipped with a stirrer, and 3.0 MPa of dilute ethylene (15 (v) %, the remainder being nitrogen) was introduced. The reactor was heated to a preset temperature using a temperature programming heating sleeve, then stirred by magnetic stirring. The reaction was carried out for 48 hours at a temperature of 250° C., and the conversion rate of methylfuran was 93% and the selectivity of toluene was 95%, as calculated based on gas phase analysis of the reaction solution.

Example II-31

In this example, n-heptane was used as a reaction solvent, the mass ratio of n-heptane to methylfuran was 20, the mass ratio of methylfuran to catalyst was 0.25, the reaction temperature was 240° C., and the reaction time was 20 h. 3.2 g of the Sn—SCM-14 molecular sieve of the above Example II-1, 0.8 g of methylfuran and 16 g of n-heptane were charged into a high-pressure reactor equipped with a stirrer, and 2.0 MPa of dilute ethylene (15 (v) %, the remainder being nitrogen) was introduced. The reactor was heated to a preset temperature using a temperature programming heating sleeve, then stirred by magnetic stirring. The reaction was carried out for 20 hours at a temperature of 240° C., and the conversion rate of methylfuran was 95% and the selectivity of toluene was 90%, as calculated based on gas phase analysis of the reaction solution.

To more intuitively describe the reaction conditions and results of Examples II-21 to II-31 above, the operation parameters and results are listed in Table 2.

TABLE 2

Catalysis results of Examples II-21 to II-31

| Example II- | Reaction solvent | Mass ratio of MF to catalyst | Mass ratio to MF to organic solvent | Reaction temperature (° C.) | Reaction time (h) | Pressure of dilute ethylene (MPa) | MF conversion (%) | Toluene Selectivity (%) |
|---|---|---|---|---|---|---|---|---|
| 21 | N-heptane | 0.8 | 20 | 240 | 20 | 2 | 91 | 94 |
| 22 | N-heptane | 2.0 | 20 | 260 | 30 | 5 | 87 | 96 |
| 23 | N-octane | 1 | 30 | 250 | 18 | 4 | 89 | 94 |
| 24 | N-octane | 1.2 | 40 | 240 | 25 | 3 | 86 | 95 |
| 25 | Tetrahydrofuran (THF) | 2 | 20 | 260 | 24 | 3 | 90 | 93 |
| 26 | Tetrahydrofuran (THF) | 1.5 | 25 | 250 | 28 | 2 | 86 | 94 |
| 27 | Methyl isobutyl ketone | 3 | 20 | 260 | 48 | 5 | 85 | 95 |
| 28 | Methyl isobutyl ketone | 1 | 40 | 250 | 20 | 2 | 89 | 94 |
| 29 | Cyclohexane | 2 | 30 | 260 | 30 | 4 | 92 | 95 |
| 30 | Cyclohexane | 1.4 | 30 | 250 | 48 | 3 | 93 | 95 |
| 31 | N-heptane | 0.25 | 20 | 240 | 20 | 2 | 95 | 90 |

Example II-32

Methylfuran was used as a substrate and n-heptane was used as a reaction solvent, 1.0 g of the Sn—SCM-14 molecular sieve of the above Example II-1, 1.0 g of methylfuran and 30 g of n-heptane were charged into a high-pressure reactor equipped with a stirrer, and 4.0 MPa of dilute ethylene (15 (v) %, the remainder being nitrogen) was introduced. The reactor was heated to a preset temperature using a temperature programming heating sleeve, then stirred by magnetic stirring. The reaction was carried out for 24 hours at a temperature of 260° C., and the reaction solution was analyzed to determine the conversion rate of methylfuran and the selectivity of the target product toluene. The spent catalyst was washed, dried and then used in the next reaction, and 4 cycles of reactions were conducted, and the results are shown in Table 3. The results show that the DMF conversion rate remained above 86% after 4 cycles of reactions, and the pX selectivity remained at 94%, indicating that the catalyst of the present application has good cycling stability.

TABLE 3

| Methylfuran conversion and toluene selectivity obtained using Sn-SCM-14 molecular sieve under cycling conditions | | |
|---|---|---|
| Number of cycles | Methylfuran conversion/% | Toluene selectivity/% |
| 1 | 90 | 96 |
| 2 | 89 | 96 |
| 3 | 88 | 95 |
| 4 | 86 | 94 |

Comparative Example II-1

An SCM-14 molecular sieve was synthesized in accordance with the method described in Example II-1 of CN109081360A, methylfuran was used as a substrate, n-heptane was used as a reaction solvent, 1.0 g of the above SCM-14 molecular sieve, 1.0 g of methylfuran and 30 g of n-heptane were charged into a high-pressure reactor equipped with a stirrer, and 4.0 MPa of dilute ethylene (15 (v) %, the remainder being nitrogen) was introduced. The reactor was heated to a preset temperature using a temperature programming heating sleeve, then stirred by magnetic stirring. The reaction was carried out for 24 hours at a temperature of 260° C., and the reaction solution was analyzed, giving a conversion rate of methylfuran of 52% and a selectivity of target product toluene of 83%.

The invention claimed is:

1. A method for preparing a substituted or unsubstituted monocyclic aromatic hydrocarbon, comprising the steps of:
contacting an organic phase comprising a substituted or unsubstituted furan as starting material with ethylene and a molecular sieve catalyst to carry out a reaction to obtain the substituted or unsubstituted monocyclic aromatic hydrocarbon,
wherein the molecular sieve catalyst comprises an SCM-X molecular sieve, the SCM-X molecular sieve being optionally doped with an element A that is at least one selected from the group consisting of Sn, Zr, and Al, and
wherein X is 14 or 15.

2. The method of claim 1, wherein the SCM-X molecular sieve has a schematic chemical composition as represented by formula "$mSiO_2 \cdot nGeO_2$", wherein $1 \leq m/n \leq 30$.

3. The method according to claim 1, wherein the organic phase comprises an organic solvent selected from the group consisting of n-hexane, n-heptane, n-octane, tetrahydrofuran, 1,4-dioxane, cyclohexane, and methyl isobutyl ketone.

4. The method according to claim 1, wherein the substituted or unsubstituted furan is of formula (I):

(I)

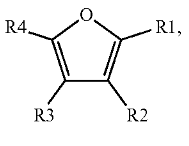

wherein R1, R2, R3, and R4 are each independently selected from the group consisting of H and C1-C6 alkyl, with a proviso that the total number of carbon atoms of R1, R2, R3, and R4 is not greater than 8.

5. The method according to claim 1, wherein the substituted or unsubstituted furan is methylfuran and the substituted or unsubstituted monocyclic aromatic hydrocarbon is toluene.

6. The method according to claim 5, wherein the SCM-X molecular sieve catalyst is an A-SCM-X molecular sieve, wherein component A in the A-SCM-X molecular sieve is at least one selected from the group consisting of Sn, Zr, and Al, and X is 14 or 15.

7. The method according to claim 6, wherein the content of component A, calculated as oxide, is not less than 0.5 wt % of a total weigh of the A-SCM-X molecular sieve, and/or
a Lewis acid content of the A-SCM-X molecular sieve is 30-500 $\mu mol \cdot g^{-1}$, and/or
a ratio of Lewis/Bronst acid of the A-SCM-X molecular sieve is 0.5-10, and/or
the A-SCM-X molecular sieve is Sn-SCM-14, Sn-SCM-15, Zr-SCM-14, Zr-SCM-15, Al-SCM-14, or Al-SCM-15 molecular sieve.

8. The method according to claim 6, wherein:
the A-SCM-X molecular sieve has a schematic chemical composition represented by the formula "$mSiO_2 \cdot nGeO_2 \cdot pAO_2$", wherein $1 \leq m/n \leq 30$ and $20 \leq m/p \leq 200$, and/or
the component A is incorporated in the framework of the molecular sieve.

9. The method according to claim 5, wherein
the reaction is carried out at
a reaction temperature of 180-300° C., and/or
for a reaction time of 4-72 h, and/or
under a reaction pressure of 1-8 MPa.

10. The method according to claim 5, wherein:
the reaction is carried out in the presence of an organic solvent that is one or more selected from the group consisting of n-heptane, n-octane, tetrahydrofuran, methyl isobutyl ketone and cyclohexane, and/or
a mass ratio of methylfuran to catalyst is 0.2-8:1, and/or
a mass ratio of the organic solvent to methylfuran is 10-80:1, and/or
the ethylene is a dilute ethylene comprising 10-25 v % of ethylene and an inert gas.

11. The method according to claim 1, wherein the substituted or unsubstituted furan is 2,5-dimethylfuran and the substituted or unsubstituted monocyclic aromatic hydrocarbon is para-xylene.

12. The method according to claim 11, wherein
the SCM-X molecular sieve is an SCM-14 molecular sieve having a schematic chemical composition represented by the formula "$SiO_2 \cdot 1/nGeO_2$", wherein $n \leq 30$.

13. The method according to claim 11, wherein the reaction is carried out
under a pressure of 0.5-8 MPa,
at a reaction temperature of 160-340° C., and/or
for a reaction time of 6-64 h.

14. The method according to claim 11, wherein the reaction is carried out in the presence of an organic solvent, and the organic solvent comprises one or more selected from the group consisting of n-hexane, n-heptane, n-octane, tetrahydrofuran, 1,4-dioxane, and cyclohexane;
the mass ratio of the starting material to the catalyst is 0.5-20.0:1, and/or
the mass ratio of the organic solvent to the starting materials is 5-50:1.

15. A method for preparing para-xylene, comprising the steps of:
contacting an organic phase comprising 2,5-hexanedione and ethylene with a molecular sieve catalyst to carry out a reaction to produce para-xylene, wherein the molecular sieve catalyst comprises an SCM-X molecular sieve, and X is 14 or 15.

16. The method according to claim 15, comprising the steps of:

(1) contacting a biomass starting material with a hydrophobic hydrogenation catalyst to carry out a reaction in a two-phase solvent system comprising an organic phase and an aqueous phase, in the presence of hydrogen as a hydrogen source, and separating the resulting product to obtain the organic phase comprising 2,5-hexanedione an aqueous phase having a pH value of 6.5-8.5; and (2) contacting the organic phase comprising 2,5-hexanedione and ethylene with the molecular sieve catalyst to produce para-xylene, wherein in step (1), the aqueous phase comprises an inorganic salt dissolved therein, the anion and cation of the inorganic salt being derived from Group VIIA elements and Group IA elements, respectively; wherein the Group VIIA element is at least one selected from the group consisting of Cl and Br, and/or the Group IA element is at least one selected from the group consisting of Li, Na, and K.

17. The method according to claim 16, wherein in step (1), the organic phase comprises an organic solvent selected from 1,2-dichloroethane, 1,4-dioxane, methyl isobutyl ketone, tetrahydrofuran, γ-valerolactone, and toluene, and mixtures thereof, and/or the mass ratio of the organic solvent to the biomass starting material is 4-60, and/or the ratio of the mass of organic solvent in the organic phase to the total amount by mass of the inorganic salt and water in the aqueous phase is 2 to 16, and/or the ratio of the mass of the inorganic salt to the mass of water is 0.10 to 0.70.

18. The method according to claim 16, wherein the mass ratio of the biomass starting material to the hydrogenation catalyst used in step (1) is in a range of from 0.2:1 to 4:1, and/or in step (1), the reaction is carried out at a temperature of 160-250° C. for 4 to 36 hours, and/or under a hydrogen pressure is 0.2-5 MPa, and/or in step (1), said hydrophobic hydrogenation catalyst comprises a hydrogenation active component and a carrier; the carrier is one or more selected from the group consisting of activated carbon and graphene having hydrophobicity; the hydrogenation active component is one or more selected from the group consisting of ruthenium, platinum, and palladium, the contact angle of the hydrogenation catalyst used in step (1) with water is greater than 50°, the hydrogenation active component is present in an amount of 0.5% to 10% by mass, calculated as metal atom, based on the mass of the hydrogenation catalyst; and/or the biomass starting material used in step (1) is one or more selected from the group consisting of cellulose, inulin, cellobiose, sucrose, glucose, fructose, corn straw, corncob, pine wood, poplar wood, and beech wood.

19. The method according to claim 16, wherein the molecular sieve catalyst used in the step (2) comprises SCM-14 and M-AlPO molecular sieves, wherein M in the M-AlPO molecular sieve is at least one selected from the group consisting of Co, Mg, Zn and Sn, and the AlPO molecular sieve is at least one selected from the group consisting of AlPO-17, AlPO-5, AlPO-8, AlPO-11 and AlPO-18, wherein the metal content of the M-AlPO molecular sieve is not less than 0.2 wt %, the M-AlPO molecular sieve has a schematic chemical composition represented by the formula "$mP_2O_5 \cdot nAl_2O_3 \cdot pMO_x$", wherein: $0.5 \le m/n \le 2$, and $20 \le m/p \le 300$, x being the total number of oxygen atoms required to satisfy the valence of M, and the M-AlPO molecular sieve has the following properties: a total acid content of 100-500 $\mu mol \cdot g^{-1}$, wherein the weak acid content is not less than 55%, and the strong acid content is not greater than 35%.

20. The method according to claim 16, wherein:

the mass ratio of the molecular sieve catalyst used in step (2) to the biomass starting material used in step (1) is from 0.1 to 5; and/or during step (1), no acid is added to the reaction system.

21. The method according to claim 15, wherein the SCM-X molecular sieve is an SCM-14 molecular sieve having a schematic chemical composition represented by the formula "$SiO_2 \cdot 1/nGeO_2$", wherein $n \le 30$, and the reaction is carried out under ethylene pressure of 0.5-5 MPa; and/or at a reaction temperature of 160-340° C.; and/or for a reaction time of 6-64 h.

* * * * *